(12) United States Patent
Driesen et al.

(10) Patent No.: US 8,813,292 B2
(45) Date of Patent: Aug. 26, 2014

(54) ELECTRIC TOOTHBRUSH AND BRUSH HEAD FOR AN ELECTRIC TOOTHBRUSH

(75) Inventors: Georges Driesen, Weilrod (DE); Michael Schmid, Frankfurt am Main (DE); Norbert Schaefer, Frankfurt am Main (DE); Hansjoerg Reick, Cincinnati, OH (US); Stefan Schamberg, Usingen (DE); Eva Susanne Thurnay, Frankfurt am Main (DE); Rory McGarry, Frankfurt am Main (DE)

(73) Assignee: Braun GmbH, Kronberg (DE)

( * ) Notice: Subject to any disclaimer, the term of this patent is extended or adjusted under 35 U.S.C. 154(b) by 389 days.

(21) Appl. No.: 13/098,692

(22) Filed: May 2, 2011

(65) Prior Publication Data

US 2011/0239391 A1   Oct. 6, 2011

Related U.S. Application Data

(63) Continuation of application No. PCT/IB2009/054899, filed on Apr. 11, 2009.

(30) Foreign Application Priority Data

Nov. 5, 2008   (EP) .................................... 08019330

(51) Int. Cl.
*A46B 9/04* (2006.01)
*A61C 17/22* (2006.01)

(52) U.S. Cl.
USPC ................ 15/28; 15/167.1; 15/22.1; D4/101; D4/111

(58) Field of Classification Search
CPC .............................. A46B 9/028; A61C 17/222
USPC ........ 15/28, 167.1, 180, DIG. 5; D4/104, 102
IPC .......... A61C 17/22, 17/24, 17/26, 17/32, 17/34; A46B 9/04, 13/02, 7/08
See application file for complete search history.

(56) References Cited

U.S. PATENT DOCUMENTS 6,021,538 A * 2/2000 Kressner et al. .................. 15/28
6,058,541 A * 5/2000 Masterman et al. ............... 15/28

(Continued)

FOREIGN PATENT DOCUMENTS

DE   202007017676 U1   3/2008
DE   202008004017 U1 *  6/2008   ............... A46B 9/04

(Continued)

OTHER PUBLICATIONS

International Search Report for PCT/IB2009/054899, dated Feb. 25, 2010.

*Primary Examiner* — Joseph J Hail
*Assistant Examiner* — Marc Carlson
(74) *Attorney, Agent, or Firm* — John P. Colbert

(57) ABSTRACT

A brush head for an electric toothbrush is disclosed. The brush head includes a bristle support having mounting means for the movable mounting of the bristle support and a plurality of bristle tufts arranged on the bristle support in at least one outer ring and one middle ring, the middle ring being nested within the outer ring and having a central area. The outer ring includes outer bristle tufts having an elongated tuft cross-section, which outer bristle tufts are mounted on opposing sides of the outer ring. The middle ring includes at least two middle bristle tufts that each have a cross-section that is smaller than the cross-section of the outer bristle tufts and a central area including at least one bristled section that consists of two center bristle tufts having a cross-section larger than the cross-section of the middle bristle tufts. The center bristle tufts each having an elongated, substantially kidney-shaped form that complement each other so that the bristled section of the central area has an approximately circular, oval or elliptical structure.

14 Claims, 16 Drawing Sheets

(56) References Cited

U.S. PATENT DOCUMENTS

| | | | |
|---|---|---|---|
| D455,556 S | 4/2002 | Kling | |
| 6,446,295 B1 * | 9/2002 | Calabrese | 15/28 |
| D478,214 S * | 8/2003 | Winkler et al. | D4/104 |
| 6,735,804 B2 * | 5/2004 | Carlucci et al. | 15/28 |
| 6,786,558 B2 * | 9/2004 | Driesen et al. | 300/21 |
| 6,957,468 B2 * | 10/2005 | Driesen et al. | 15/167.1 |
| D517,325 S | 3/2006 | Black et al. | |
| 7,392,562 B2 * | 7/2008 | Boland et al. | 15/28 |
| 7,520,016 B2 * | 4/2009 | Kressner | 15/22.1 |
| D606,316 S * | 12/2009 | Driesen et al. | D4/101 |
| D606,318 S * | 12/2009 | Driesen et al. | D4/101 |
| D606,758 S * | 12/2009 | Driesen et al. | D4/101 |
| D611,711 S * | 3/2010 | Driesen et al. | D4/101 |
| 7,810,199 B2 * | 10/2010 | Kressner | 15/22.1 |
| 7,962,991 B2 * | 6/2011 | Hohlbein | 15/110 |
| 8,166,601 B2 * | 5/2012 | Brown et al. | 15/201 |
| 2001/0023516 A1 * | 9/2001 | Driesen et al. | 15/167.1 |
| 2002/0108194 A1 * | 8/2002 | Carlucci et al. | 15/28 |
| 2002/0138926 A1 * | 10/2002 | Brown et al. | 15/22.1 |
| 2002/0166188 A1 | 11/2002 | Driesen et al. | |
| 2004/0130203 A1 * | 7/2004 | Driesen et al. | 300/21 |
| 2005/0060822 A1 * | 3/2005 | Chenvainu et al. | 15/28 |
| 2005/0272002 A1 * | 12/2005 | Chenvainu et al. | 433/80 |
| 2006/0282963 A1 * | 12/2006 | Brown et al. | 15/28 |
| 2008/0172814 A1 * | 7/2008 | Brown et al. | 15/28 |
| 2011/0179594 A1 * | 7/2011 | Zini | 15/167.1 |
| 2011/0179595 A1 * | 7/2011 | Chenvainu et al. | 15/167.1 |
| 2011/0247154 A1 * | 10/2011 | Driesen et al. | 15/22.1 |
| 2011/0296642 A1 * | 12/2011 | Driesen et al. | 15/167.1 |
| 2012/0019046 A1 * | 1/2012 | Driesen et al. | 300/21 |
| 2012/0036654 A1 * | 2/2012 | Driesen et al. | 15/21.1 |
| 2012/0227201 A1 * | 9/2012 | Brown et al. | 15/167.1 |
| 2013/0007968 A1 * | 1/2013 | Driesen et al. | 15/22.1 |
| 2013/0007969 A1 * | 1/2013 | Driesen et al. | 15/28 |

FOREIGN PATENT DOCUMENTS

| | | | |
|---|---|---|---|
| EP | 0835081 B1 | 4/1998 | |
| EP | 1806065 A1 * | 7/2007 | A46B 9/04 |
| WO | WO 01/60281 A | 8/2001 | |
| WO | WO 0160281 A1 * | 8/2001 | |
| WO | WO 02/054975 A | 7/2002 | |
| WO | WO 2004/000155 A | 12/2003 | |
| WO | WO 2004000155 A1 * | 12/2003 | A61C 17/22 |

* cited by examiner

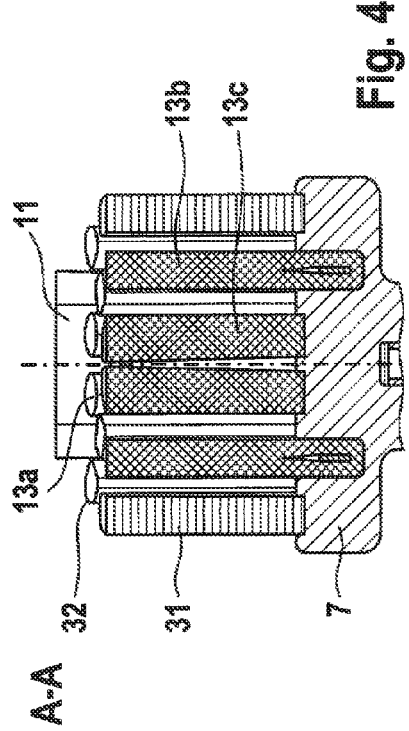
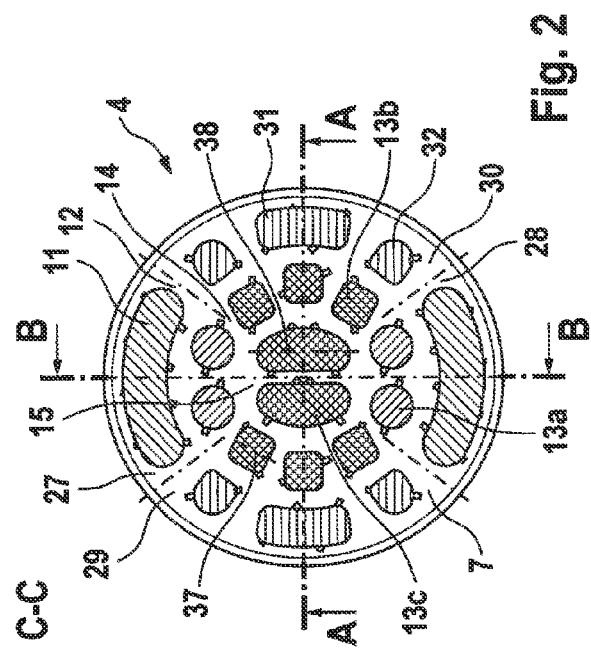
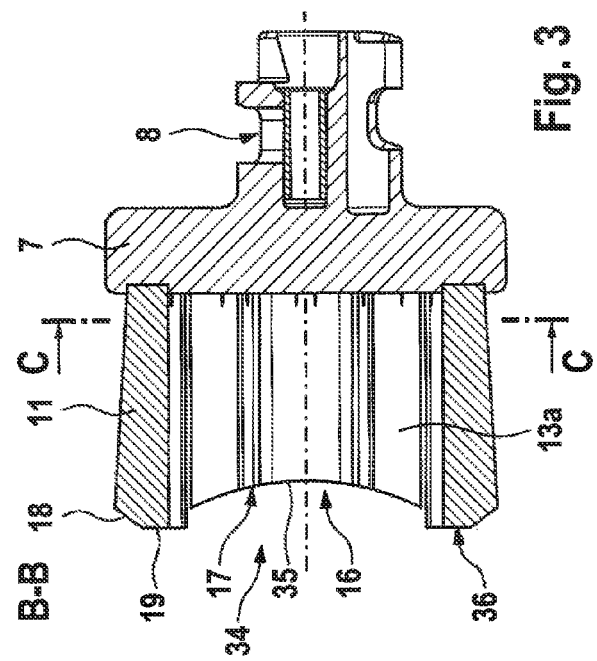

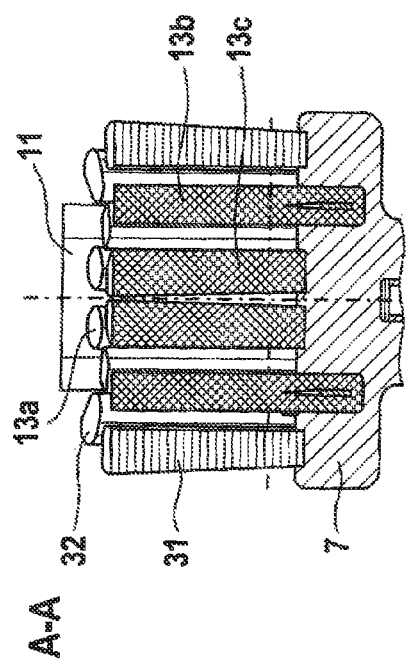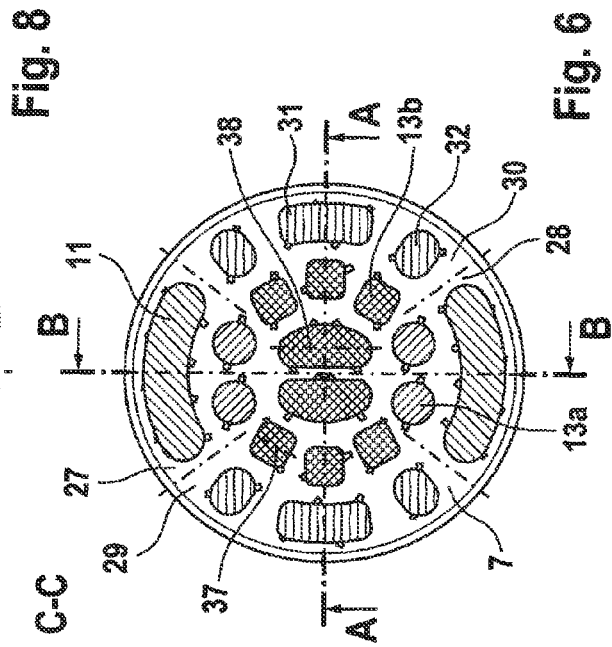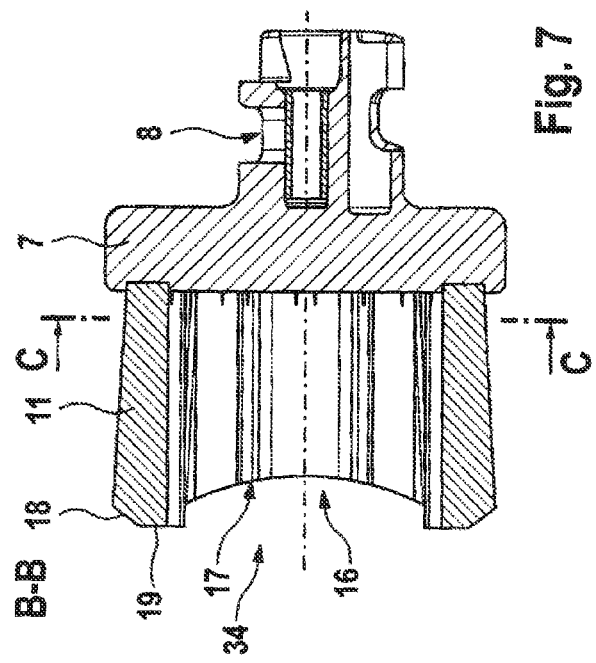

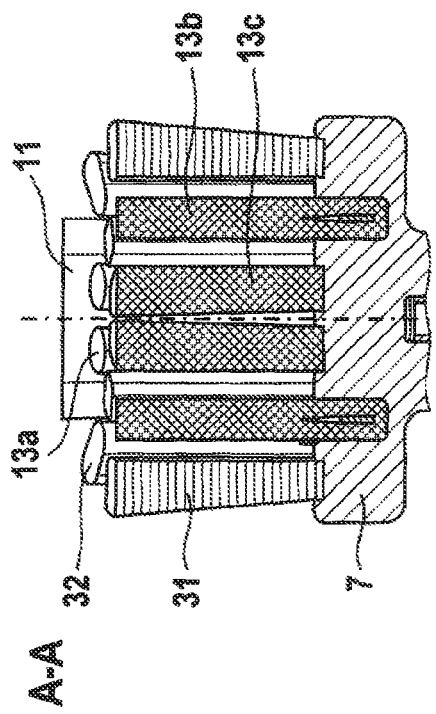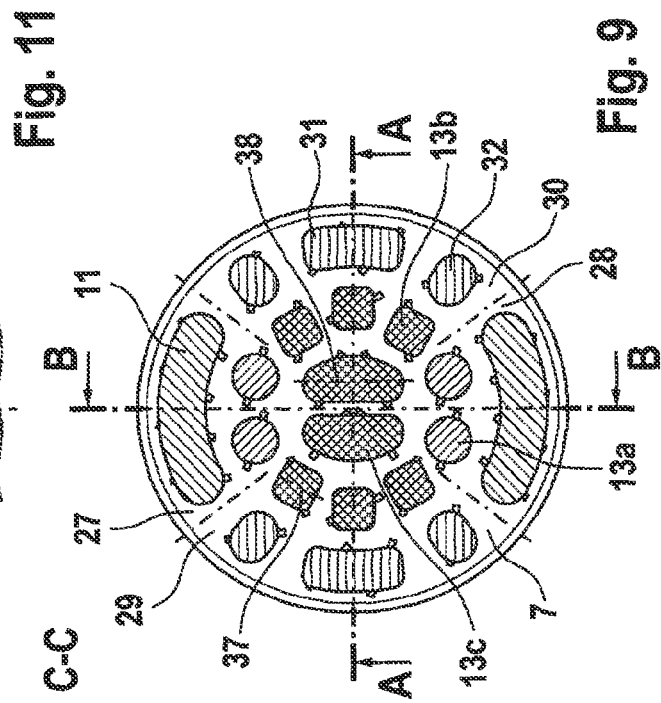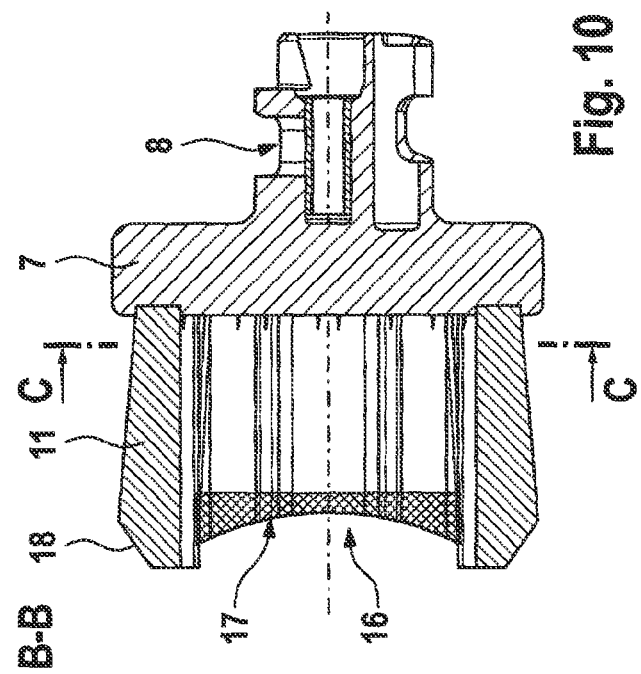

ELECTRIC TOOTHBRUSH AND BRUSH HEAD FOR AN ELECTRIC TOOTHBRUSH

CROSS REFERENCE TO RELATED APPLICATIONS

This application is a continuation of International Application No. PCT/IB2009/054899, filed Apr. 11, 2009, which claims priority to EP 08019330.3 filed Nov. 5, 2008, the substance of which is incorporated herein by reference in its entirety

FIELD OF THE INVENTION

The present disclosure relates to an electric toothbrush and more particularly to a drivable brush head for an electric toothbrush having a bristle support including mounting means for the movable mounting of the bristle support as well as a plurality of bristle tufts arranged on the bristle support.

BACKGROUND OF THE INVENTION

With drivable bristled sections it is at times difficult to achieve a high bristle density on the bristle support, particularly when it is desired to secure the bristle tufts to the bristle support using a technique referred to as anchor tufting. In one example, drivable bristle supports of electric toothbrushes have a relatively small surface area for focusing the driving motion on the tooth surfaces—in particular when the drive performs an oscillatory rotational motion. In another example, special tuft configurations are desired on drivable bristled sections. For example, round bristle supports which are oscillated in a rotary motion are frequently fitted with power tips in the area of the toothbrush longitudinal axis, i.e., toothbrush tufts which are of a greater height and protrude beyond the other tufts so as to enable them to penetrate into interproximal spaces. Such bristle tufts on the outer circumference of the bristle support conveniently have an elongated contour with a narrow, longitudinally extended tuft cross-section, thereby enabling the interproximal cleansing effect to be improved in addition to enabling the dentifrice applied to the bristled section to be held better on the working surface.

Disclosed, for example, in EP 0835081 B1 are tufts which are arranged on the circumference of a circular, rotationally drivable bristled section in the region of the longitudinal axis and project beyond the tufts arranged further inside. While such extended tufts on the outer circumference of the bristled section indeed enable the cleansing effect on the interproximal spaces to be enhanced, the cleaning action on the tooth flank sections adjoining the interproximal spaces fails to be optimal as yet. On the other hand, such configurations of bristled sections cannot be moved really gently from one tooth to another, so that brushing motions of the brush head in the toothbrush longitudinal direction produce a prodding sensation.

Similarly constructed brush heads, which are rotationally drivable and include a central recess or depression in the working surface of the bristled section, are known from US-D 478,214, US-D 517,325 or US-D 455,556.

The provision of elongated bristle tufts on the outer circumference of the bristled section aggravates the aforementioned problem of being able to achieve a high bristle density on the bristle support when affixing the tufts by means of the anchor tufting technique, since such elongated bristle tufts have to be affixed with several anchor wires with corresponding space demands.

Proceeding from the foregoing, it is a desire to provide an improved electric toothbrush and an improved brush head therefore, which prevent the disadvantages of the prior art while developing the art further in advantageous manner. In particular, it is desirable to achieve a high bristle density on the bristle support without foregoing the possibility of securing the bristle tufts by the anchor tufting technique.

SUMMARY OF THE INVENTION

In one embodiment, a brush head for an electric toothbrush is provided. The brush head includes a bristle support having mounting means for the movable mounting of the bristle support and a plurality of bristle tufts arranged on the bristle support in at least one outer ring and one middle ring, the middle ring being nested within the outer ring and having a central area. The outer ring includes outer bristle tufts having an elongated tuft cross-section, which outer bristle tufts are mounted on opposing sides of the outer ring. The middle ring includes at least two middle bristle tufts that each have a cross-section that is smaller than the cross-section of the outer bristle tufts and a central area including at least one bristled section that consists of two center bristle tufts having a cross-section larger than the cross-section of the middle bristle tufts. The center bristle tufts each having an elongated, substantially kidney-shaped form that complement each other so that the bristled section of the central area has an approximately circular, oval or elliptical structure.

In another embodiment, a brush head for an electric toothbrush is provided. The brush head includes a substantially plate-shaped bristle support including mounting means for the moveable mounting of the bristle support and a majority of bristle tufts arranged on the bristle support in at least one outer ring and one middle ring, the middle ring being nested within the outer ring and having a central area. The outer ring includes elongated bristle tufts of an elongated tuft cross-section, which elongated bristle tufts are mounted on opposing sides of the outer ring. The middle ring includes several bristle tufts each of a cross-section smaller than the cross-section of the elongated bristle tufts of the outer ring and a central area including at least one bristled section that consists of bristle tufts, formed by bristle ends, with a cross-section larger than the cross-section of the bristle tufts of the middle ring.

In another embodiment, a brush head for an electric toothbrush is provided. The brush head includes a bristle support having mounting means for the movable mounting of the bristle support and a plurality of bristle tufts being arranged on the bristle support. A central area of the bristle support includes at least one bristled section that consists of two center bristle tufts having a cross-section larger than the cross-section of middle bristle tufts adjoining the central area. The center bristle tufts each having an elongated, substantially kidney-shaped form that complement each other so that the bristled section of the central area has an approximately circular, oval or elliptical structure.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

FIG. 2 is a top plan view of the brush head of the toothbrush of FIG. 1;

FIG. 3 is a longitudinal sectional view of the brush head taken along the line B-B of FIG. 2 parallel to the longitudinal axis of the toothbrush;

FIG. 4 is a longitudinal sectional view of the brush head of FIG. 2 taken along the line A-A of FIG. 2;

FIG. 6 is a schematic top plan view of the brush head of the toothbrush of FIG. 1 according to another embodiment shown and illustrated herein;

FIG. 7 is a longitudinal sectional view of the toothbrush head taken along the line B-B of FIG. 6 parallel to the longitudinal axis of the toothbrush;

FIG. 8 is a longitudinal sectional view of the brush head taken along the line A-A of FIG. 6;

FIG. 9 is a schematic top plan view of the brush head of the toothbrush of FIG. 1 according to another embodiment shown and illustrated herein;

FIG. 10 is a longitudinal sectional view of the toothbrush head taken along the line B-B of FIG. 9 parallel to the longitudinal axis of the toothbrush;

FIG. 11 is a longitudinal sectional view of the brush head taken along the line A-A of FIG. 9;

DETAILED DESCRIPTION OF THE INVENTION

Figure 1:
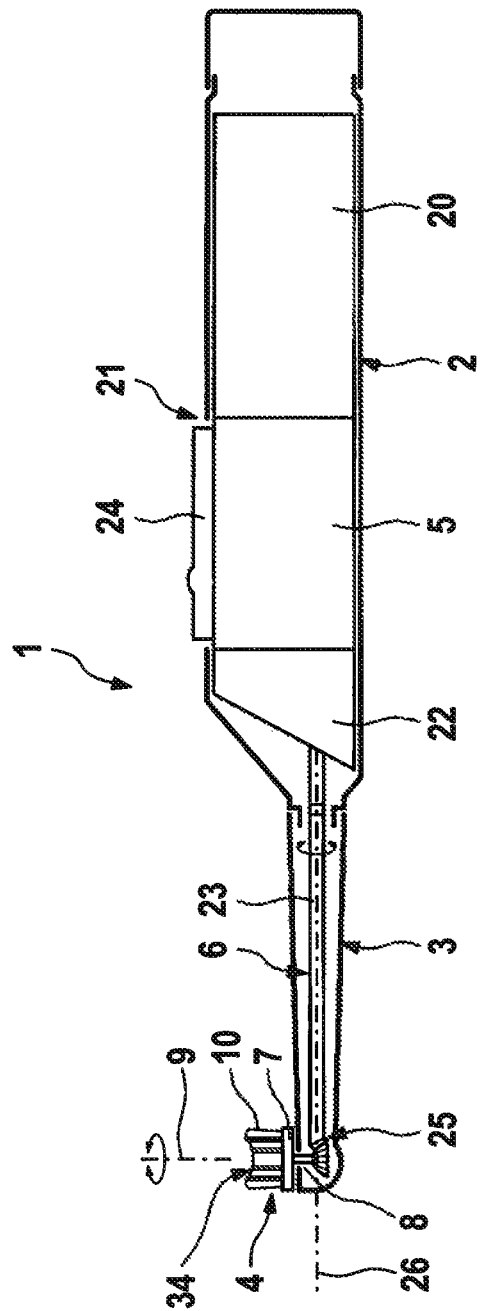
FIG. 1 is a schematic side view of an electric toothbrush having a rotationally drivable brush head according to an embodiment shown and illustrated herein.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, a brush head that comprises a bristle support that has mounting means for movable mounting of the bristle support is provided. The bristle support is approximately plate-shaped. In an embodiment, the mounting means are arranged so that a rotating oscillatory movement of the bristle support is provided. A plurality of bristle tufts is arranged on the bristle support. In one embodiment, the bristle support has a central area that includes a bristled section that consists of two center bristle tufts that have a cross section larger than the cross section of middle bristle tufts that are arranged adjoining the central area. The center bristle tufts have an elongated form, for example, they have an approximately half-moon like shape or a banana-like shape or a kidney-like shape, but it should not be excluded that the center tufts are linearly extending tufts. The two center tufts are arranged such that their cross-sectional forms complement each other so that the bristled section in particular has an approximately circular, oval or elliptical structure (which structure may be defined by a convex enveloping area that comprises the two center bristle tufts). Generally, the lateral dimensions of the bristled section formed by the two center bristle tufts are such that a first lateral width measures between about 50% and about 100% of a second lateral width being perpendicular to the first lateral width, in particular, the first lateral width measures about 70% to about 90% of the second lateral width.

It is to be noted that the phrase "bristle tuft" is not necessarily to be understood as a single tuft of filaments that are fixed to the bristle support in a single step (for example, by anchor tufting) but relates to bristle tufts that appear as essentially a single bristle tuft even though they may have been composed in a multi-step process where several small bristle tufts are composed to form a larger sized bristle tuft ("compound bristle tuft"). It is also to be noted that the (tuft) cross section of a bristle tuft is defined in a plane parallel to the bristle tuft carrying surface of the bristle support, where it is assumed that compound bristle tufts appear as single bristle tufts.

In accordance with a further embodiment, the plurality of bristle tufts arranged on the bristle support is provided in rings or regions that are nested within each other. Thus, an outer ring or region exists on which outer bristle tufts are mounted and a middle ring or region exists, which middle ring or region is nested within the outer ring, on which the middle bristle tufts are mounted. In this embodiment, the outer bristle tufts have an elongated tuft cross section and the outer bristle tufts are arranged on opposing sides of the outer ring or region. Further, the middle bristle tufts have a cross section that is smaller than the cross section of the outer bristle tufts. In this embodiment, the central area comprising the two center bristle tufts as explained is provided in a center of the middle ring or region and the middle bristle tufts adjoining the central area have a smaller cross section than the outer bristles tufts and the centre bristle tufts.

In one embodiment, large sized center bristle tufts yields an improved stability of the central area of the brush head during operation. Usually, the user pushes the central area of the brush head against the tooth surface and the bristles of the central area will bend under the applied force if the bristle density (tuft stability) is too low, which in turn leads to reduced cleaning efficacy. The proposed center bristle tufts that have together an approximately circular, oval or elliptical cross-sectional structure provide enough stability to each other so that a bending of the bristles of the central area is efficiently avoided. The presence of smaller sized middle bristle tufts around the center bristle tufts allows yielding a high density of bristle tufts on the bristle carrier. The further provision of elongated outer bristle tufts does not only further support a high bristle density on the bristle carrier but also provides stability for the whole bristle field on the circumferential border of the overall bristle tuft field. The presence of large sized center bristle tufts leads to high bristle density and high central stability in accordance with one embodiment. The presence of middle bristle tufts and outer bristle tufts as proposed that are provided in nested rings or regions yield high bristle density and circumferential stability within a further embodiment.

In an embodiment, the bristled area within an enveloping circular area that comprises the two center tufts rates to at least between about 40% to about 80% of the enveloping circular area. In another embodiment, the bristled area covers at least a fraction of about 50% of the enveloping circular area and in another embodiment the bristled area is at least about 60%. In another embodiment, the enveloping circular area is between about 5% to about 15% of the overall area of the bristle support. In yet another embodiment, the enveloping circular area is between about 7% to about 9% of the area of the bristle support.

In a further embodiment, the middle bristle tufts have cross-sectional areas of approximately equal size. This allows a relatively simple manufacturing as all middle bristle tufts can be mounted using the same tufting machine. In an even further embodiment, each bristle tuft of the plurality of bristle tufts (comprising the outer bristle tufts, the middle bristle tufts and the center bristle tufts) has a cross sectional area that is approximately identical to a base area or is an integer multiple of the base area. In this case, all bristle tufts can be mounted using the same tufting machine, where the larger sized bristle tufts are assembled from two or more base bristle tufts that are mounted side-by-side in an elongated mounting hole and thus form compound bristle tufts.

In other words, in the central area an increased packing density of bristles (or bristle tufts) is provided, which form a central tooth engagement area and, as a result of the bristle density, prevent further sinking in along the bristle length. This increased density at bristle ends of a central bristled section is obtainable by a plurality of directly adjoining bristle tufts (having a distance of less than about 1.5 mm, or in another embodiment about 1 mm) The bristle tufts mounted in the central area are combined to form two larger sized compound bristle tufts (which however require more than one anchor tufting wire for their securing) and/or the center bristle tufts which, proceeding from the plate-shaped bristle support, may be inclined towards each other, so that the bristle ends form a dense bristled section substantially without any tufting gap. Thus, a high density of bristle ends in the central bristled section is achievable by any one of the above measures or any desired combination of the above three approaches.

It is thus proposed to concentrate bristle tufts of a large cross-sectional area at the circumferential outer edge of the bristle support (outer bristle tufts) and in its central area (center bristle tufts) and further to provide tufts of a small cross-sectional area between these large-area bristle tufts at the edge and in the center on a middle ring of tufts (middle bristle tufts), and to avoid collision of the tuft fastening means by selection of the cross-sectional geometries and their relative orientation even in cases where the bristles are densely packed. According to one embodiment, within the elongated outer bristle tufts on the outer ring there are arranged on a middle ring several middle bristle tufts of a cross-section smaller than the cross-section of the elongated tufts, and within these smaller tufts on the middle ring there are provided at least two tufts with a cross-section larger than the cross-section of the tufts on the middle ring. By virtue of this rhythmic alternation of tuft cross-sections from inside to outside, a high bristle density is achievable and a collision of the fastening means is better avoidable. In addition, advantages result with regard to the cleaning effect. It will be understood that the bristles can be provided also in combinations other than bristle tufts. Any reference to the bristle tufts can therefore be regarded alternatively as a reference to a majority of bristles according to this disclosure, as described above and below and in the claims. Moreover, other types of dental cleaning elements can be used alternatively in lieu of bristles. Furthermore, the bristle tufts as described in this context can be arranged on relatively arranged outer, middle or inner regions instead of on outer, middle and inner rings.

Among other things, the dentifrice usually applied in the center of the bristled section is held better on the working surface.

In a further embodiment, middle bristle tufts of varying cross-sectional shapes are arranged on the at least one middle ring of bristles. In particular on the at least one middle ring middle bristle tufts may be provided which have an approximately square tuft cross-section. Alternatively or in addition, the middle ring may also include middle bristle tufts with a round cross-section, in particular a circular cross-section. If angular, in particular square, and round, in particular circular bristle tufts are arranged on the middle ring, they are advantageously concentrated in different sectors each. To do this, a variety of options exist in general. According to one embodiment, round middle bristle tufts are arranged on the middle ring in opposing sectors, which in the non-deflected neutral position of the bristle support contain the toothbrush longitudinal axis. By contrast, the angular bristle tufts of the middle ring are advantageously arranged in opposing sectors of the bristle support which in the bristle support's neutral position are arranged symmetrically to a transverse axis.

In one embodiment, in order to provide favorable space conditions for the securing of the bristle tufts, the angular bristle tufts of the middle ring, at least some of them, are turned at an acute angle relative to the main axes of the bristle support and also relative to the annular contour of the ring on which they are arranged. In one embodiment, at least one of the angular bristle tufts, in another embodiment every second angular bristle tuft, may have its main axis turned in such a way that the main axis of the bristle tuft cross-section is inclined at an acute angle to a tangent to the middle ring. As a result, corresponding anchor plates are turned out of the collision range of other anchor plates. In addition, the flexing behavior of the bristled section can be made more homogeneous on the whole and in particular less dependent on direction.

Regardless of their different cross-sectional shapes, the bristle tufts of the middle ring have at least by approximation roughly the same area of cross-section, with the areas of cross-section varying in a range of less than about +/−25%, in another embodiment less than about +/−10% and in yet another embodiment less than about +/−3%. Compared to the areas of cross-section of the bristle tufts of the middle ring, the outer, elongated bristle tufts on the outer ring as well as the at least two innermost centre bristle tufts in the central area have an area of cross-section at least twice as large.

In this embodiment, on the outer ring of the bristled section there may be arranged several opposite lying pairs of elongated outer bristle tufts. For improved adaptation of the bristle configuration to the different cleaning tasks in different areas of the bristled section, the outer ring may include differently designed pairs of elongated bristle tufts which differ in respect of their bristle length and/or height and/or cross-sectional area. Various configurations are generally possible in this context. According to an embodiment, opposing sectors of the bristle support, which in its non-deflected neutral position contain the toothbrush longitudinal axis, include longer bristle tufts and/or elongated bristle tufts of greater cross-sectional area than the tufts in sectors oriented at right angles thereto in a direction transverse to the toothbrush longitudinal axis.

In addition to the elongated outer bristle tufts, the outer ring may provide further outer bristle tufts of a not elongated contour, which may have an approximately round or square cross-section of a cross-sectional area smaller than the cross-sectional area of the elongated bristle tufts. In a further embodiment, the central area of the bristled section includes two equally elongated center bristle tufts whose longitudinal axis, that is, the longitudinal dimension of the elongated cross-section, is aligned parallel to a main axis of the bristle support. In one embodiment, the innermost bristle tufts may have their longitudinal axes oriented parallel to the toothbrush longitudinal axis in the non-deflected neutral position of the bristle support and/or oriented towards the elongated bristle tufts of the outer ring which on the outer ring have the greatest height and/or greatest cross-sectional area.

The bristle support and/or the bristled section formed on the bristle support may generally have various outer contours, with the bristle support being advantageously of a round configuration in particular when driven rotationally. In another embodiment, however, the bristle support is not circular but of a shape deviating from the circular form. For example, the bristle support may be of an oval or elliptical configuration or slightly flattened in a similar way. Alternatively or in addition, at least the outer row or the outer ring of bristle tufts may be arranged on an oval or on an ellipse or on a ring flattened in similar manner.

As seen looking at the top of the bristle support, the bristle tufts may be arranged symmetrically relative to the main axes of the bristle support and/or rotationally symmetrically, for example, in such a way that the bristle tufts or their points of attachment on the bristle support are transformable one into the other by a turn through 180 degrees. Alternatively or in addition, the bristled section may however have an asymmetrical contour as seen in a side view, for example, in a direction transverse to the toothbrush longitudinal axis, particularly in such a way that the height profile rises more intensively towards one side than towards the other side.

In a further embodiment, the bristled section has a central depression in the working surface defined by the free ends of the bristle tufts, which advantageously may have a groove-shaped bottom curved in one direction and substantially straight in the direction perpendicular thereto. Through such a substantially uniaxially curved depression in a middle portion of the bristled section or its working surface, it is possible to achieve not only a better holding of the dentifrice or a similar, gel-type dental cleansing agent but above all a better cleaning effect on the teeth accompanied by a more agreeable, gentler cleaning sensation. The contour of the working surface, which rises to opposing circumferential sides, nestles better against the lateral tooth flanks which, so to speak, are enveloped in a snug fit so that in particular the sections of the tooth flanks adjoining the interproximal spaces are better cleaned.

Unlike bristled sections with plane depressions in the middle, it is not necessary for the innermost, i.e., middle and center bristle tufts, to bend away first. Rather, the middle center bristle tufts rest in a snug fit against the lateral flanks of the teeth without bending away. In addition, a gentler cleaning sensation results, in particular when moving the brush head from one tooth to the next, because due to the varying tuft height also in the central region individual tufts are pushed away in succession when the brush sweeps over a tooth flank, the brush head being pushed, so to speak, along the curved surface of the depression around the flank of the next tooth without the brush head falling into the depression. For example, with rotational driving of the bristled section there results in addition a gentle wiping motion because the tufts hugging the tooth flank are more intensively bent as the distance from the axis of rotation increases.

The groove-shaped curvature of the depressed, central portion of the bristled section surface can be achieved generally in a variety of ways. For example, a correspondingly curved bristle support could be provided while the tufts are of uniform length. However, in a further embodiment, the tufts and the inner lying tufts may vary in their length such that they define with their free ends the groove-shaped curvature. For example, the length of the inner lying tufts can increase in the direction of the curvature of the working surface defined by the free ends with increasing distance from a center point of the bristle support, such as to define said groove-shaped curvature of the central depression. Through such a varying length of the tufts it is possible to achieve a gentle cleaning sensation and a gentle movement of the bristled section over the teeth because the further projecting bristles are able to bend away more easily on account of their greater length.

In order to obtain a most continuous curvature of the surface of the central depression, the free ends of the inner tufts, which define said working surface in the region of the depression, do not have end surfaces extending parallel to the bristle support but end surfaces which are inclined at an acute angle to the surface of the bristle support, with different inner tufts having differently inclined end surfaces, such that the differently inclined end surfaces define in mutual complementation the path of said groove-shaped contour of the central depression. For example, the inclination of the end surfaces of the free ends of the tufts can be made increasingly more pronounced as the distance of the tufts from the center of the bristle support increases, thus resulting in an increasingly steeper wall of the groove-shaped bottom in the direction of the circumferential edges of the bristled section.

Generally, the tufts may form a plane surface at their free ends. In this case the inner tufts define the groove-shaped curvature so to speak in the form of a chine-type construction with a slant increasing in steps from tuft to tuft. However, in another embodiment, the free ends of the inner tufts can have at their free ends an end surface which is not plane but arcuately curved such that the mutually complementing free ends of neighboring tufts define a continuously curved enveloping surface which forms the previously mentioned groove-shaped depression. The curved end surfaces of the individual tufts are advantageously uniaxially curved, i.e., they are in themselves already curved in groove shape, so that they run in a straight line in one direction while having a curvature in a direction perpendicular thereto.

The groove-shaped curved bottom of the central region of the working surface of the bristled section can be generally of a symmetrical configuration, i.e., extending substantially parabolically. In this case the inner tufts rise with their free ends at a substantially equal rate to opposing circumferential sides of the bristled section.

In a further embodiment, an asymmetric path of the curvature of the central depression in the working surface of the bristled section may be provided, in which case a banana-shaped groove curvature can be provided. In this arrangement, the tufts defining the central depression in the working surface of the bristled section rise unequally to opposing circumferential sides so that the one upper edge of the groove-shaped depression is higher than the opposing edge. Among other things, this can be used, for example, to compensate for the tendency of users to position the brush head against the tooth flanks in a not exactly tangential but alternatively in a slightly V-shaped orientation.

To achieve an even more greatly improved interproximal cleaning effect, in a further embodiment, longer or higher tufts have at least one bevel on their free end surfaces. For example, the lateral edges of the end surfaces can be beveled in the manner of a chamfer. On the one hand said longer outer bristle tufts can better penetrate into the interproximal spaces. On the other hand the brush head can be moved more easily and more gently from one tooth to the next because the bevels of the circumferentially outer lying tufts raise the bristled section so to speak in the manner of a wedge-shaped inclined surface onto the next tooth flank. In this example, the outer, longer tufts can be generally beveled towards both the inner side and the outer side. However, in another embodiment, only one bevel is provided on one of the sides of the respective tuft so that a sufficiently wide, non-beveled end surface remains, as a result of which a cleaning effect is achieved equally in the interproximal spaces and on the tooth flanks.

In a further embodiment, the outer edges of the free ends of the tufts, i.e., the edges facing away from the inner tufts, are beveled. As a result, the brush head can be pushed particularly gently from one tooth to the next. Alternatively or in addition, the inner-side edge of the end surface of said outer, longer tufts can also be beveled. As a result, the working surface of the bristled section rests with a particularly snug fit against the round-bodied tooth flanks. The inner-side bevel is a continuation, so to speak, of the groove-shaped curved depression in the center of the working surface of the bristled section. Alternatively or in addition, the inner-side edge of the end surface of said outer, shorter tufts—in a direction transverse to the longitudinal direction of the brush—can also be beveled. This enhances the cleaning effect in the gingival-tooth area.

Depending on the application and configuration of the tufts, the bevel on the circumferential, longer tufts can be variously pronounced. A good cleaning effect both between the teeth and on their surfaces can be achieved when said bevel of the circumferential tufts is inclined at an angle of approximately from about 20° to about 60°, in another embodiment from about 25° to about 40°, relative to the non-beveled end surface of said tuft. Generally, the depth of the bevel can be variously selected, with an advantageous compromise between easy entry into the interproximal spaces and remaining cleaning capability on the tooth flanks being accomplished if said bevel extends over approximately from about 25% to about 75% of the width of the tuft at its end. In this context, "width" is understood to mean the dimension of the tuft vertically to its longitudinal axis and transversely to the longitudinal direction of the bevel.

Particularly effective are the circumferential, longer outer bristle tufts, for example, in combination with the bevels, when the tufts are inclined at least with their outer side towards the outer circumferential side at an acute angle relative to a vertical on the bristle support, and this at an angle in the range from about 1.5° to about 15°, in another embodiment from about 3° to about 10°, approximately. As a result the tufts acquire a reduced resistance to buckling in one direction during the to and fro motion of the brush head, thus giving rise to better insertion into the interproximal spaces.

In a further embodiment, the longer outer bristle tufts have a cross-sectional area that grows larger towards their free ends and/or lateral flanks that spread apart as they progress from the bristle support. In particular the circumferential outer bristle tufts can be trapezoidally shaped as seen in a longitudinal sectional view, such that the free ends of the tuft are wider than its base on the bristle support. In one example, such a trapezoidal configuration lends the tufts a larger working surface on their free ends. In another example, the fan-type spreading apart enables the bristles within a tuft to move relative to each other with greater ease, which results on the whole in a better adaptation to the tooth contour and an improved cleaning performance. For example, with lateral bevels of the free ends of the tufts, said tufts acquire favorable geometrical proportions with more tangible edges which nestle better against the boundary contours of the teeth.

The trapezoidal configuration of the outer, longer tufts is advantageously asymmetric in relation to a vertical on the bristle support. For example, an inner flank of the tufts, which faces the inner tufts, can extend substantially vertically to the surface of the bristle support while an outer side of the respective tuft, which faces away from the inner tufts, is inclined towards the outer side at an acute angle to a vertical on the bristle support. Accordingly, the outer flanks stand-off outwardly at an angle while the inner flanks stand straight, that is, they are aligned substantially vertically to the bristle support surface.

On the elongated bristle tufts, the previously mentioned bevel on the free end of the tuft extends advantageously parallel and/or tangentially to the longitudinal axis of the elongated end surface of the tuft. In a further embodiment, longer outer bristle tufts are provided on the outer circumference in opposing circumferential sectors on opposing circumferential sides so that the central depression in the working surface of the bristled section extends between the opposing longer circumferential tufts. In this arrangement, the longer, outer bristle tufts are advantageously not provided along the entire circumference of the bristled section but only in limited angular sectors of less than about 60° per sector angle, whereas no longer, elevated outer bristle tufts are positioned circumferentially in intermediate sectors in which the groove-shaped curved depression in the central region is at its deepest. The groove-shaped central depression extends, so to speak, transversely across the entire bristled section. In the sectors in which the groove-shaped depression is at its deepest, the outer circumferential tufts are adapted to the configuration of the groove-shaped depression contour or they form part of it.

The brush head can be generally driven in a variety of ways. Different drive kinematics can be implemented depending on the configuration of the toothbrush and its drive. In one embodiment, the driving motion comprises an oscillatory rotational motion about an axis of rotation which extends through the bristle support. In one embodiment, the axis of rotation can extend vertically to the plane of the bristle support through its center point or center of gravity. However, according to an alternative embodiment, it is also possible for the axis of rotation to be positioned eccentrically so that motion components of different magnitude are generated on different circumferential sides of the bristled section. In a further embodiment, the eccentricity applies to the longer, outer bristle tufts, that is, the axis of rotation is displaced parallel to a connecting line through the opposing, outer, longer tufts. Depending on the configuration of the bristled section, the eccentricity can be variously pronounced, with a good compromise between cleaning movements of desirably different size on different circumferential sides on the one hand and still tolerable vibrating movements on the other hand being achieved when the axis of rotation divides a diameter line of the bristle support in a length ratio of from about 55% to about 45% up to from about 70% to about 30%.

Alternatively or in addition, it is possible for the axis of rotation of the bristle support to be inclined at an acute angle to the plane defined by the support, with the angle of inclination being in the range from about 89° to about 65°, in another embodiment from about 88° to about 82°, relative to the plane of the bristle support. As a result it is possible, in conjunction with the groove-shaped curved surface profile of the bristled section, to superimpose a poking motion upon the rotary motion. In one embodiment, the axis of rotation is tilted such that the bristled section is tilted away from the handpiece of the toothbrush. This enables better access to difficult-to-clean tooth areas, in particular regarding the molars and the inner surfaces of the incisors.

Given a rotary oscillation of the bristled section, in a further embodiment, the end surface of the circumferentially outer, longer tufts, which looks elongated in the plan view, extends in an arc about the axis of rotation, for example, in a circular arc about the axis of rotation.

In a further embodiment, the previously mentioned bevels on the outer ends of the longer, outer bristle tufts can nevertheless extend in a straight line, for example, substantially tangentially to the arcuately curved, elongated end surface of the tufts. In one example, this simplifies the production of the tufts. In another example, this results in a circumferentially varying width of the bevels and, concomitant thereto, of the non-beveled end surfaces, which in the manner of wedge surfaces can cause the corresponding tufts to be continuously inserted into and withdrawn from the interproximal spaces.

However, according to an alternative embodiment it is also possible for the bevels to extend equally in an arcuate curve around the axis of rotation, in particular such that the bevels and/or the remaining, non-beveled end surfaces of the tufts have a contour and width that is constant in circumferential direction. As a result, it is possible to achieve a particularly gentle contacting of the tufts with the tooth flanks and a favorable or uniform penetration into the interproximal spaces. In one embodiment, the outer, longer tufts enclose the inner tufts along a distance covering from about 25% to about 75%, approximately, of the circumference of the bristled section or the bristle support.

The inner tufts, which with their free ends define said central depression in the working surface, can form with their free ends a substantially continuous surface such that an in actual fact continuous groove-shaped depression results. In one example, it is thus possible to achieve a nestling around the full surface of the tooth flanks and hence a cleaning effect covering a large area. In another example, it has a beneficial effect on the positioning of the dentifrice or the tooth cleaning agent, which is held better on the working surface of the bristled section and does not flow so easily between the tufts down onto the bristle support.

In another embodiment, the inner tufts can form with their free ends separate end surfaces, as a result of which a better discharge of dislodged debris is achievable.

The exemplary electric toothbrush 1 shown in FIG. 1 comprises a handle section 2 and a brush head 4 adapted to be detachably coupled to it. The brush head 4 comprises a neck section 3 of the toothbrush 1 connected to the handle section 2, said neck section 3 being constructed in the form of a partly hollow tube. The handle section 2 accommodates in its interior an energy source 20, for example, a rechargeable battery, a motor 5, for example, an electric motor, and a control device 21.

In the embodiment shown, the rotary motion of the motor 5 is translated by means of a gearing 22 into an oscillatory rotational motion of a drive shaft 23 which extends through the neck section 3 to the distal end of the brush head 4. The toothbrush 1 can be activated and deactivated with a switch 24 mounted on the handle section 2.

In known manner using a suitable gearing (for example, a bevel gearing 25), at the end of the drive shaft 23 a bristle carrier 7 is drivable into an oscillatory rotational motion about an axis of rotation 9 which extends substantially in a direction transverse to the toothbrush longitudinal axis 26. As this occurs, the angular range swept by the bristle support 7 of the brush head 4 has a value of about ±35°±5°, with an oscillation in the range from about ±10° to about ±100° being also possible. The oscillation frequency can vary and lie, for example, between about 10 Hz and about 100 Hz. In the embodiment shown in FIG. 1, the axis of rotation 9 forms a right angle with the toothbrush longitudinal axis 26. In addition, a drive of the brush head 4 is provided in a third dimension for its pulsing motion in the direction of the axis of rotation or oscillation.

An exemplary embodiment of a brush part for use in the brush head 4 of the toothbrush 1 is shown in FIGS. 2 to 5. In this embodiment, the bristle support 7 is round, however not circular (even though a circular shape is not excluded) but slightly oval and/or elliptical, with the longer axis of the oval or the ellipse in the neutral position of the bristle support 7 extending parallel to the toothbrush longitudinal axis 26, and the shorter axis of the oval or the ellipse extending in a direction transverse to it. In FIG. 2 the longer axis of the oval or the ellipse is parallel to the line B-B.

Arranged on the bristle support 7 is a plurality of bristle tufts which are arranged in several approximately circular or non-circular rings 12 and 14 and spread over the bristled section 10. Positioned on an outer ring 12 in the embodiment of FIG. 2 are eight tufts, of which four have an elongated contour while another four have a generally round or equilateral cross-sectional contour. The length of the tufts on said outer ring 12 varies, as will be explained in more detail, with generally longer tufts being provided in opposing sectors 27 and 28, which in the initial position of the bristle support 7 contain the toothbrush longitudinal axis 26, than in sectors 29 and 30, which are orientated in a direction transverse thereto or lie in between, as shown in FIG. 2.

As FIG. 2 shows, the tufts 11 and 31 lying on the outer ring 12 on the main axes B-B and A-A, respectively, are elongated in the plan view while the tufts 32 lying in between have an approximately equilateral contour or an approximately cubic or round cross-section. Said elongated tufts 11 and 31 extend in an arcuate curve around the axis of rotation 9, as shown in FIG. 2. In this arrangement, the outer bristle tufts 11 sitting on the longer main axis B-B extend over a circumferential section of from about 50° to about 90°, in another embodiment about 70°, while the outer bristle tufts 31 sitting on the shorter main axis A-A extend over a circumferential section of from about 20° to about 45°, in another embodiment about 30°.

Positioned on a middle ring 14 of tufts, seen from the outside, are a total of ten tufts 13a and 13b, of which some have a circular cross-section and others an angular cross-section. In particular tufts 13a with a circular cross-section are arranged, as shown in FIG. 2, in the sectors 27 and 28 in which the longer outer bristle tufts 11 of the outer ring 12 lie, while angular tufts are provided in the intermediate sectors 29 and 30 of the bristle support 7 on the second ring 14. Also, the length of these tufts 13a and 13b on the middle second ring 14 varies cyclically from tuft to tuft along the circumference of the ring 14, in such a way that longer tufts are provided in said sectors 27 and 28 than in the sectors 29 and 30 lying on the short main axis.

The round middle bristle tufts 13a as well as the angular, approximately square (or angular) middle bristle tufts 13b of the middle ring 14 have approximately at least about the same area of cross-section regardless of their different cross-sectional contour.

As FIG. 2 shows, to provide favorable space conditions for the securing of the bristle tufts, in a further aspect of the invention the angular middle bristle tufts 13b of the middle ring 14, at least some of them, may be turned at an acute angle relative to the main axes A-A and B-B of the bristle support 7 and also relative to the annular contour of the ring 14 on which they are arranged. Particularly at least one of the angular middle bristle tufts, preferably each second angular middle bristle tuft 13b, may have its main axis 37 turned in such a way that the main axis 37 of the bristle tuft cross-section is inclined at an acute angle to a tangent to the middle ring 14. This causes corresponding anchor plates to be turned out of the collision range of other anchor plates. In addition, the flexing action of the bristled section can be made more homogeneous on the whole and in particular less dependent on direction.

Finally, in an innermost region 15, that is, in a central area of middle ring 14 as seen looking from the outside, two elongated tufts 13c are provided which extend with their longitudinal dimension parallel to the longer main axis B-B.

The center bristle tufts 13c have a cross-sectional area significantly greater than the middle bristle tufts 13a and 13b of the middle ring. In the embodiment shown, their cross-sectional area amounts to between about 200% and about 400% of the cross-sectional area of the middle bristle tufts 13a and 13b of the middle ring 14.

In this arrangement, the center bristle tufts 13c are of an elongated configuration so that their longitudinal dimension 38 amounts to more than about 150% of their transverse dimension, in another embodiment from about 150% to about 300%, approximately. In the embodiment shown, the center bristle tufts 13c have an outer contour curved in convex shape while an inner contour is straight, with the inner and outer contours being advantageously connected by rounded end contours. Thus the overall shape of the exemplary center bristle tufts 13c is approximately banana-shaped. The two approximately half-moon shaped centre bristle tufts 13c are arranged in a way that their shapes complement each other so that they together form an approximately oval bristled section. In general, the shape of the two center bristle tufts may be approximately half-moon shaped or banana-shaped or kidney-shaped and they may be arranged such that their shapes complement each other to form a generally round, for example, circular, oval or elliptical bristled section defined by an enveloping, convex curve drawn around the two centre bristle tufts.

The center bristle tufts 13c as shown have their longitudinal axes 38 aligned parallel to the main axis of the bristle support which in the non-deflected neutral position of the bristle support 7 extends parallel to the toothbrush longitudinal axis 26 or a longitudinal center plane passing therethrough. The tufts form with their bristle ends a substantially homogeneous, densely packed bristle end surface. This is achieved by the provision of tufting hole walls 13d which are inwardly inclined towards the axis of rotation at an angle of about 1° to about 2°, thereby causing the central bristle tufts to be inclined towards each other.

As FIG. 3 shows, the tufts of the bristled section 10 have their free ends contoured or coordinated with each other with regard to their length and/or height, such that the working surface 34 of the bristled section 10 as defined by the free ends of the tufts has a central depression 16 with a groove-shaped bottom 17 which is curved in one direction and straight in a direction vertical to it. The curvature extends advantageously in the direction of the longer main axis B-B or in the direction of the toothbrush longitudinal axis 26 when the bristle support 7 is in its non-deflected neutral position. In a direction perpendicular thereto, which extends parallel to the shorter main axis A-A of the bristle support 7 and/or transversely to the toothbrush longitudinal axis 26 when the bristle support 7 is in its non-deflected neutral position, the depression 16 has a straight contour as shown in FIG. 4.

The central depression 16 can be constructed to be variously deep. In one embodiment, the deepest point of the depression 16 is set an amount of approximately from about 1 mm to about 3 mm, in another embodiment about 2 mm, deeper than the highest point of the bristled section 10. The groove-shaped contour of the bottom 17 of the depression 16 generally can have different curvatures. In the embodiment shown in FIGS. 3 to 5, a circular-arc-shaped contour with a curvature radius in the range from about 8 mm to about 17 mm, in another embodiment from about 10 mm to about 14 mm and in yet another embodiment about 12 mm, is provided, but this can vary depending on the dimensions and configuration of the bristled section.

As FIG. 3 shows, the end surfaces of the inner bristle tufts 13a, 13b and 13c and the end surfaces of the shorter, outer bristle tufts 31, which likewise combine to define the groove-shaped bottom 17, are not constructed as plane surfaces but are likewise in themselves curved in groove shape. The groove-shaped curved end surfaces 35 complement each other and in combination form said groove-shaped contour of the bottom 17 of the central depression 16. In concrete terms, the inclination of the end surfaces of the inner bristle tufts 13 increases as the distance from the axis of rotation 9 in the direction parallel to the main axis B-B increases, as shown in FIG. 3. In other words, the tufts arranged on the transversally extending main axis A-A are slightly curved at their free ends but nevertheless are aligned substantially parallel to the bristle support surface, while the inclination of the free ends increases as the distance from said main axis A-A increases.

As FIG. 3 also shows, the outer bristle tufts 11 arranged on the outer ring 12 in sectors 27 and 28 are extended relative to the other tufts or have a greater height such that they project beyond the other tufts. This results in a step in height relative to the central depression 16, as shown in FIG. 3, that is, the central depression 16 in the embodiment shown in FIG. 3 does not merge smoothly with the end surfaces of said outer bristle tufts 11.

The outer bristle tufts 11 in the opposing sectors 27 and 28, which in the neutral position of the bristle support contain the toothbrush longitudinal axis 26, have end surfaces 36 that comprise a flat section 19, which is aligned substantially vertically to the longitudinal axis of the tufts 11, as well as bevels 18, which bevel said end surfaces 36 towards the outside.

Figure 5:
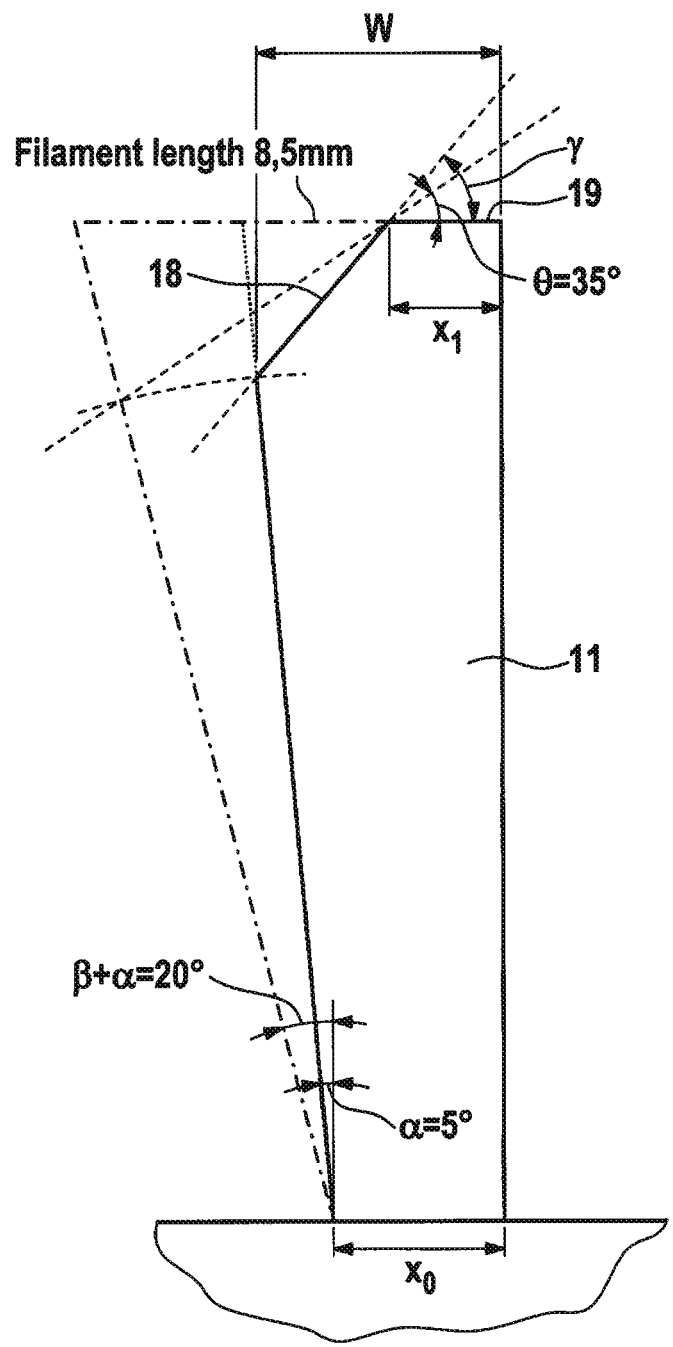
FIG. 5 is an enlarged side view of one of the outer, longer bristle tufts of FIG. 3 in an enlarged schematic representation showing the bevel angles of the tuft.

As FIG. 5 shows, said bevels 18 extend at an angle γ in the range from about 20° to about 60°, in another embodiment from about 30° to about 40°. In one embodiment, the bevels 18 are so deep and wide as to cover from about 25% to about 75% of the width W of the respective tuft 11. In this case the width W is understood to be the dimension of the tuft vertically to its longitudinal axis and vertically to the longitudinal dimension of the bevel 18, in the region of the free end of the tuft, as shown in FIG. 5. In the embodiment shown in FIG. 5, the bevel extends over approximately ¼ to ¾ of the width W (measured along the longitudinal axis B-B).

The longer outer bristle tufts 11 are on the whole of a trapezoidal configuration as seen in their longitudinal section. While the inner lying flank of the tuft 11 extends substantially vertically to the plane defined by the bristle support 7, the outer lying flank is inclined towards a vertical on the bristle support 7 at an angle α of from about 1.5° to about 10°, in another embodiment from about 3° to about 5°, such that the cross-section of the tuft 11 increases towards its free end, that is, the tuft becomes wider towards its free end. As a result, a large working surface is obtainable with a limited size of the bristle support 7. In addition, favorable geometrical proportions result at the free end of the tuft 11 in relation to its bevel 18.

In order to embrace the tooth flanks as completely as possible, to distribute the brushing pressure over a wide area and to hold dentifrice or the like on the working surface 34, the tufts occupy with their free ends at least from about 35% to about 55%, in another embodiment about 50% or more of the area defined by the bristle support 7. As FIG. 2 shows, the tufts on the outer ring 12 can extend over a circumferential section of from about 200° to about 300°, when the extension of all tufts is added together. The second ring 14 of tufts, seen from the outside, can extend likewise over a circumference of from about 200° to about 300°, when the extension of all tufts along the circumference is added together. The innermost tufts can cover with their free ends advantageously an area substantially closed over its full surface.

The embodiment of the brush head 4 shown in FIGS. 6 to 8 corresponds substantially to that of FIGS. 2 to 5 so that reference is made to the corresponding preceding description in order to avoid duplicate descriptions. The embodiment of FIGS. 6 to 8 differs substantially from that of FIGS. 2 to 5 only in the somewhat deeper contour of the central, groove-shaped depression 16, which is curved with a smaller radius of curvature, and in an on the whole round contour of the non-elongated tufts 32 on the outer ring 12 of tufts.

The other embodiment of the brush head 4 of FIGS. 9 to 11 corresponds substantially to the embodiment of FIGS. 6 to 8 so that reference is made to its preceding description. Unlike said previous embodiment, the longer outer bristle tufts 11 in the sectors 27 and 28 of the bristle support 7, which in its non-deflected neutral position contain the toothbrush longitudinal axis 25, have more pronounced bevels 18, which are beveled at an angle γ of about 55° relative to the flat sections 19 of the end surfaces 36 in order to permit an even better penetration of these tufts 11 into interproximal spaces.

In one example, some and/or all of the inner bristle tufts 13, in particular the inner bristle tufts 13b and 13c, which with their free ends define the groove-shaped bottom of the central depression 16, have their free ends specially constructed. Said tufts 13b and 13c are comprised at least partly of filaments whose ends are fanned out so that, so to speak, a soft pile and/or fleece is produced at the free ends, as a result of which dentifrice is well held particularly in this region and the tufts nestle around the tooth surface over almost its full area.

Figure 12:
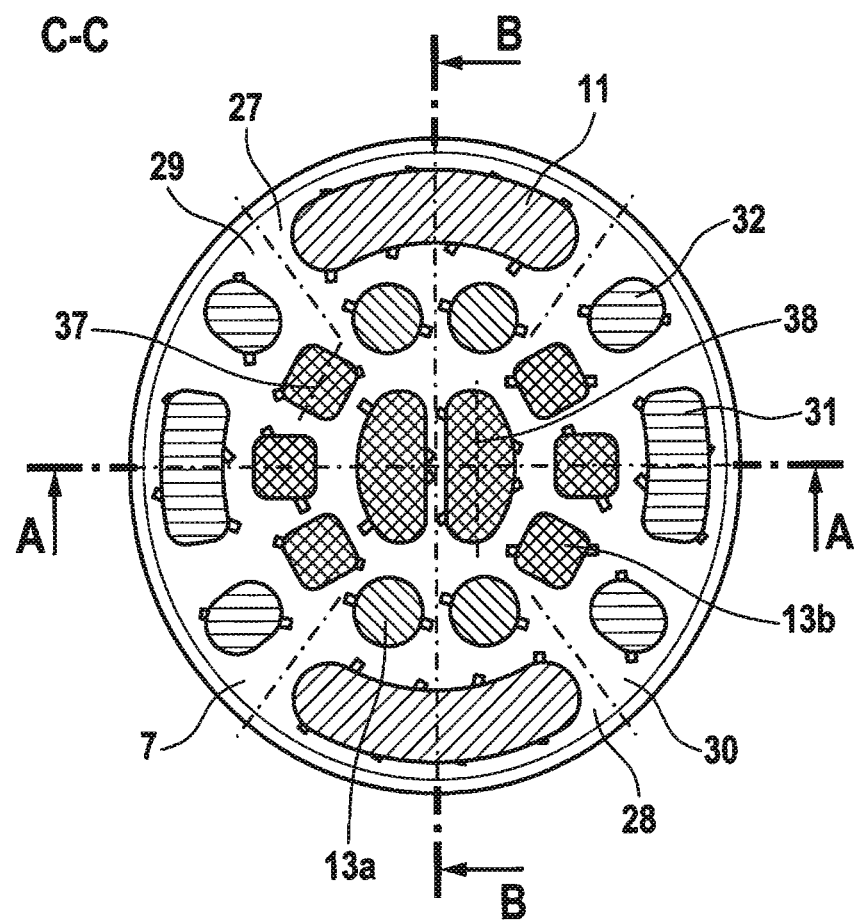
FIG. 12 is a schematic top plan view of the brush head of the toothbrush of FIG. 1 according to another embodiment shown and illustrated herein.
Figure 13:
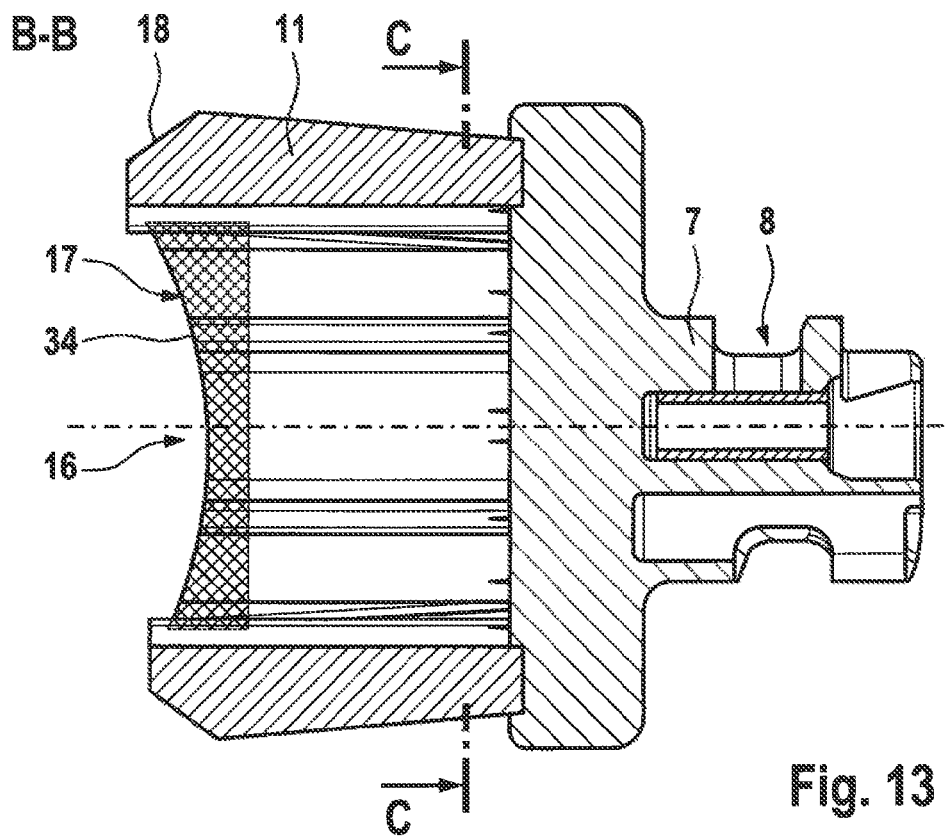
FIG. 13 is a longitudinal sectional view of the toothbrush head taken along the line B-B of FIG. 12 parallel to the longitudinal axis of the toothbrush.
Figure 14:
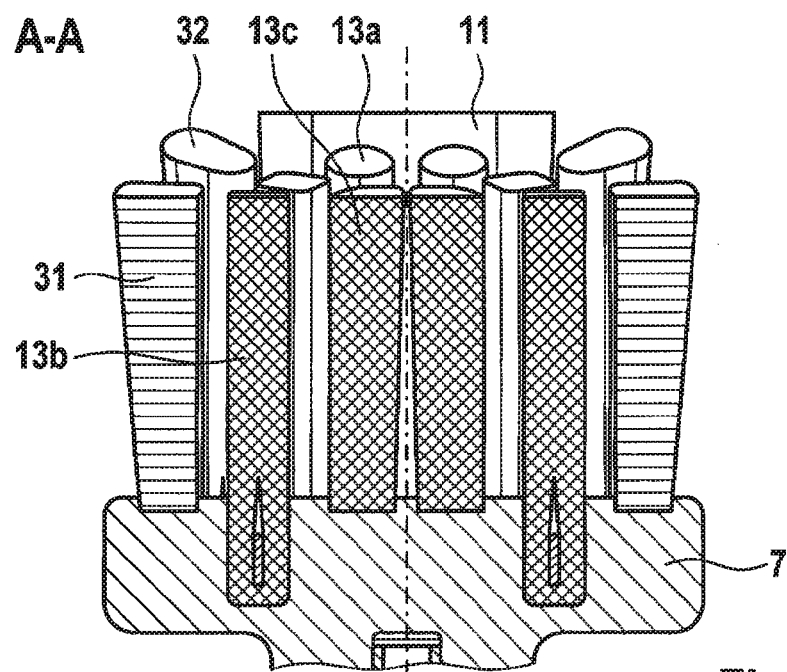
FIG. 14 is a longitudinal sectional view of the brush head taken along the line A-A of FIG. 12.

The embodiment shown in FIGS. 12 to 14 corresponds substantially to the embodiment of FIGS. 9 to 11 so that reference is made to its preceding description. Unlike this preceding embodiment, the maximum difference in height between the deepest point of the depression 16 and the highest point of the bristled section is bigger and amounts to about 2 mm, approximately, for the same curvature of the bottom 17 of the depression 16. The bristles in the region of the sectors 27 and 28 differ in length. This enables better access to the molars and the inner tooth surfaces of the incisors. In addition, the outer inclination of the bristles is between about 3° and about 5°.

Figure 15:
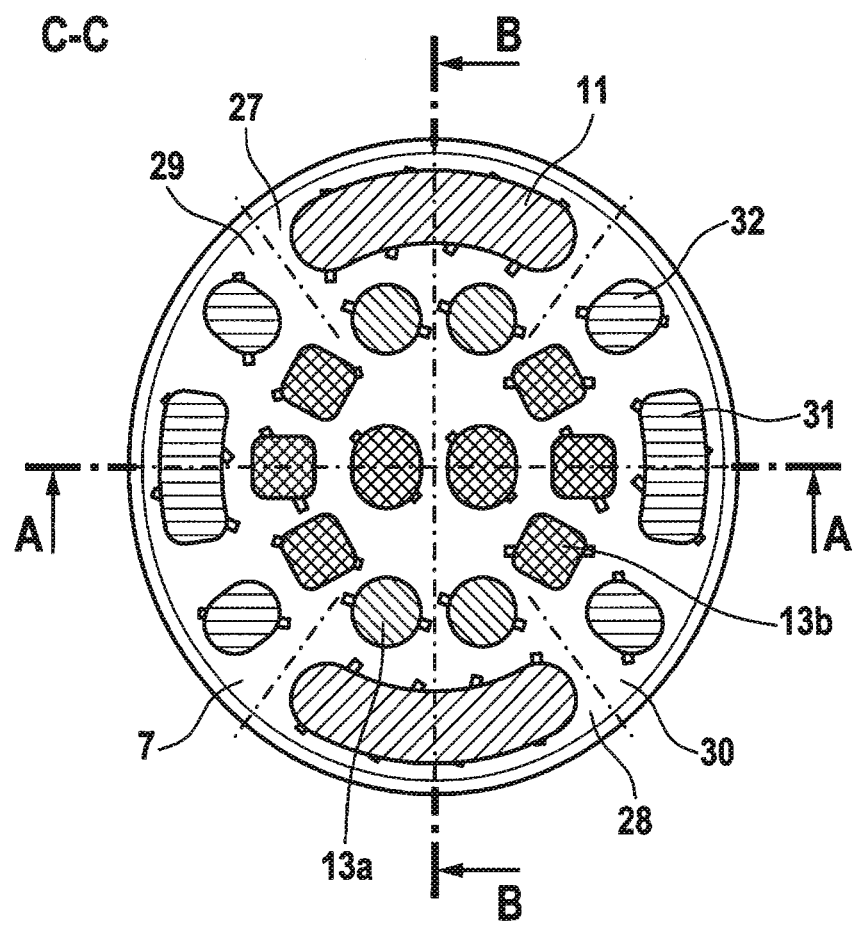
FIG. 15 is a schematic top plan view of the brush head of the toothbrush of FIG. 1 according to another embodiment shown and illustrated herein.
Figure 16:
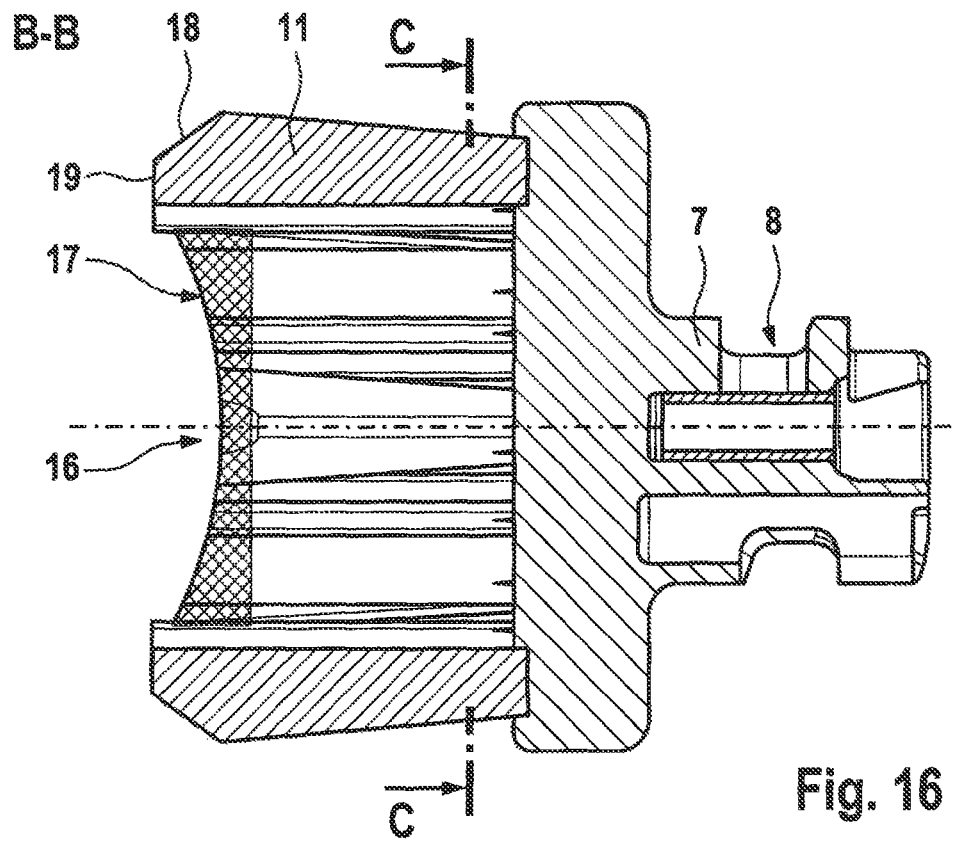
FIG. 16 is a longitudinal sectional view of the toothbrush head taken along the line B-B of FIG. 15 parallel to the longitudinal axis of the toothbrush.
Figure 17:
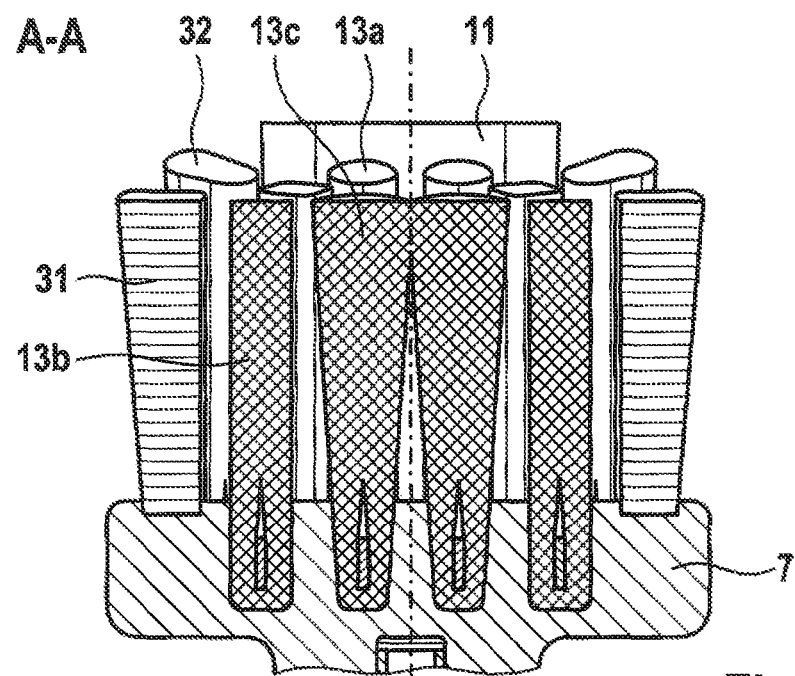
FIG. 17 is a longitudinal sectional view of the brush head taken along the line A-A of FIG. 15.

The other embodiment of the brush head 4 of FIGS. 15 to 17 corresponds substantially to the preceding embodiment of FIGS. 12 to 14 so that reference is made to its preceding description. Unlike this preceding embodiment, the innermost ring 15 of the bristle support 7 includes two less greatly elongated tufts 13c which substantially have a slightly oval cross-section and are orientated with their longitudinal axes parallel to the main axis B-B. However, as FIG. 17 shows, said innermost tufts 13c are widened with a more pronounced taper so that their cross-section increases towards the free ends. As FIG. 17 shows, the innermost tufts 13 flare at an opening angle in the range from about 0° to about 10°, in another embodiment from about 1.5° to about 5°, such that in the region of the free ends the two tufts 13c unite and form a joint surface while at the foot end on the bristle support 7 they are spaced from one another.

Figure 18:
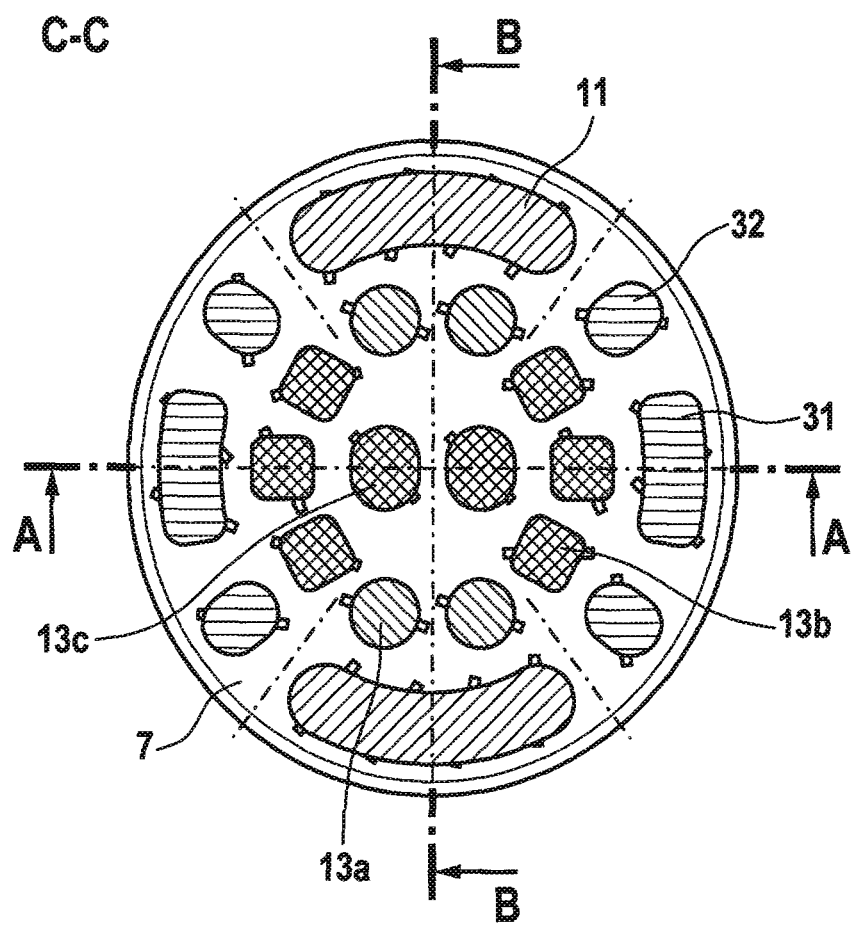
FIG. 18 is a schematic top plan view of the brush head of the toothbrush of FIG. 1 according to another embodiment shown and illustrated herein.
Figure 19:
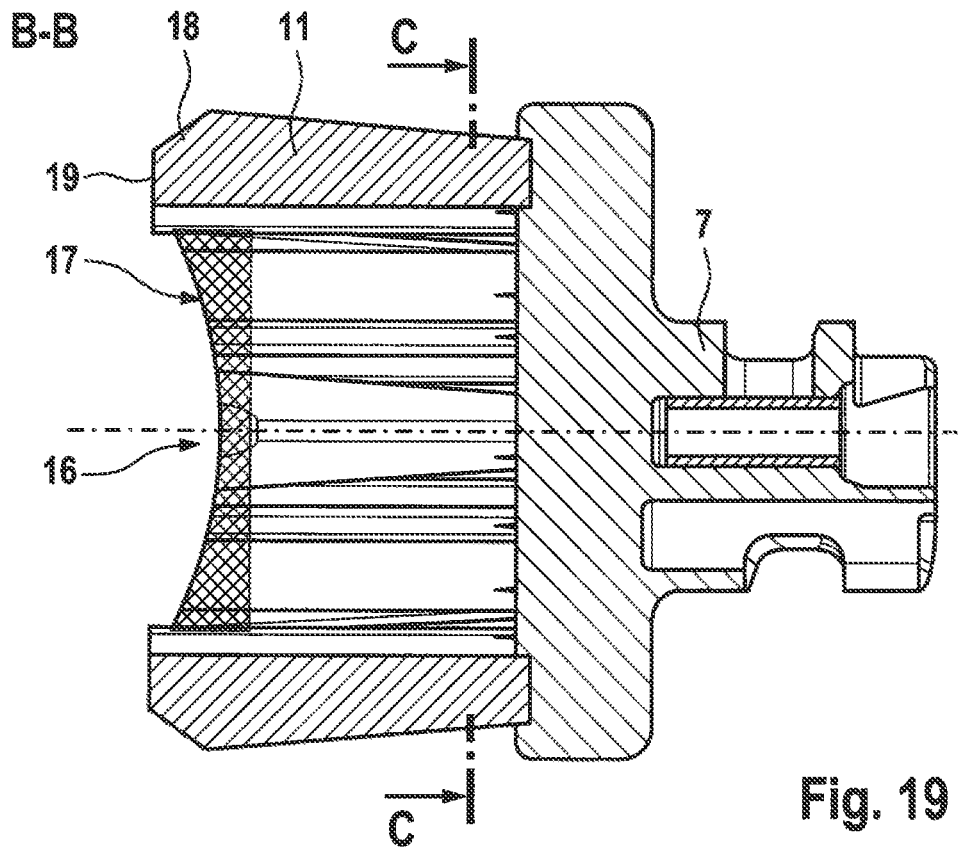
FIG. 19 is a longitudinal sectional view of the toothbrush head taken along the line B-B of FIG. 18 parallel to the longitudinal axis of the toothbrush.
Figure 20:
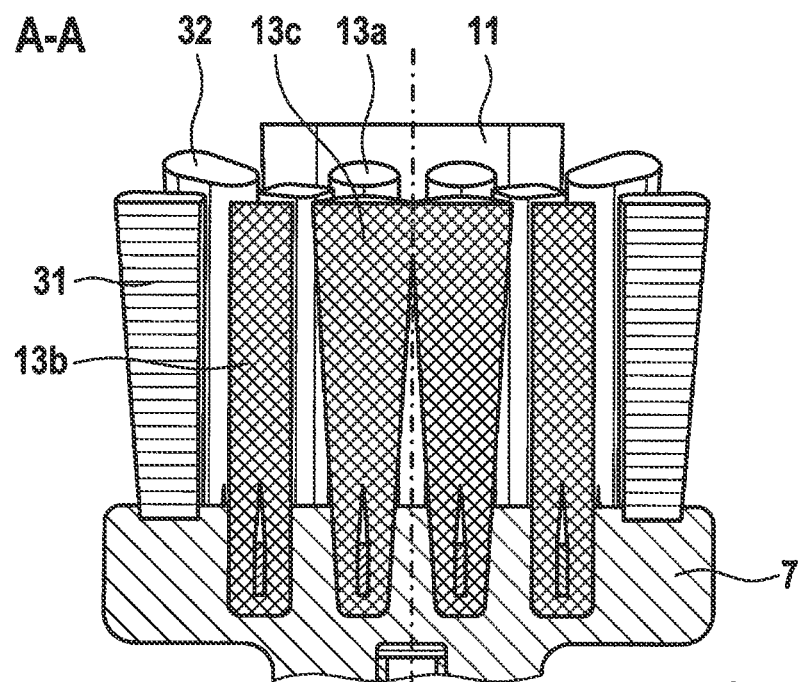
FIG. 20 is a longitudinal sectional view of the brush head taken along the line A-A of FIG. 18.

The embodiment of FIGS. 18 to 20 corresponds substantially to the preceding embodiment of FIGS. 15 to 17 so that reference is made to its preceding description. However, unlike the preceding embodiment the bevels 18 of the elevated, outer bristle tufts 11 in the sectors 27 and 28 are of a different configuration. While the bevels 18 of the preceding embodiments extended in a straight line, that is, in spite of the arcuate shape of the tufts 11 as seen in the plan view they defined a plane surface, the bevels 18 of the embodiment of FIGS. 18 to 20 are arcuately curved, with the bevels 18 being likewise curved around the axis of rotation 9 in accordance with the curved shape of the tufts 11, such that a substantially uniform beveling of the tufts 11 results. More accurately speaking, the tufts 11 are beveled by the same amount substantially along their entire length, that is, their dimension in the circumferential direction, because the bevel 18 follows the shape of the tufts 11. This configuration can also be applied to all other embodiments described.

Figure 21:
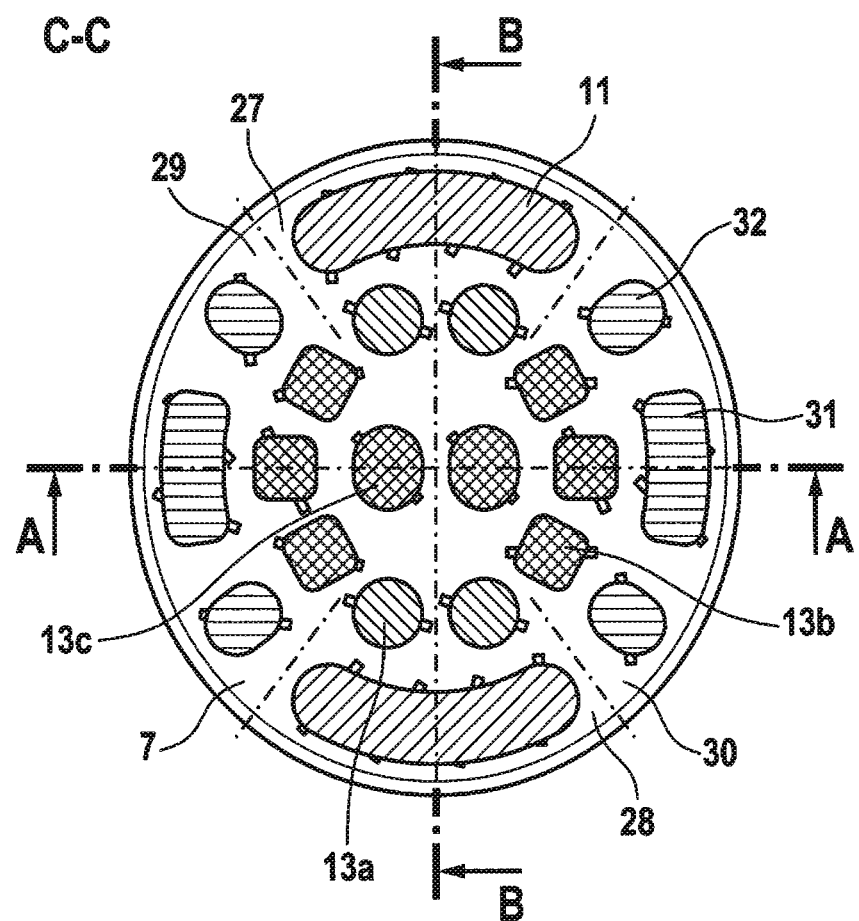
FIG. 21 is a schematic top plan view of the brush head of the toothbrush of FIG. 1 according to another embodiment shown and illustrated herein.
Figure 22:
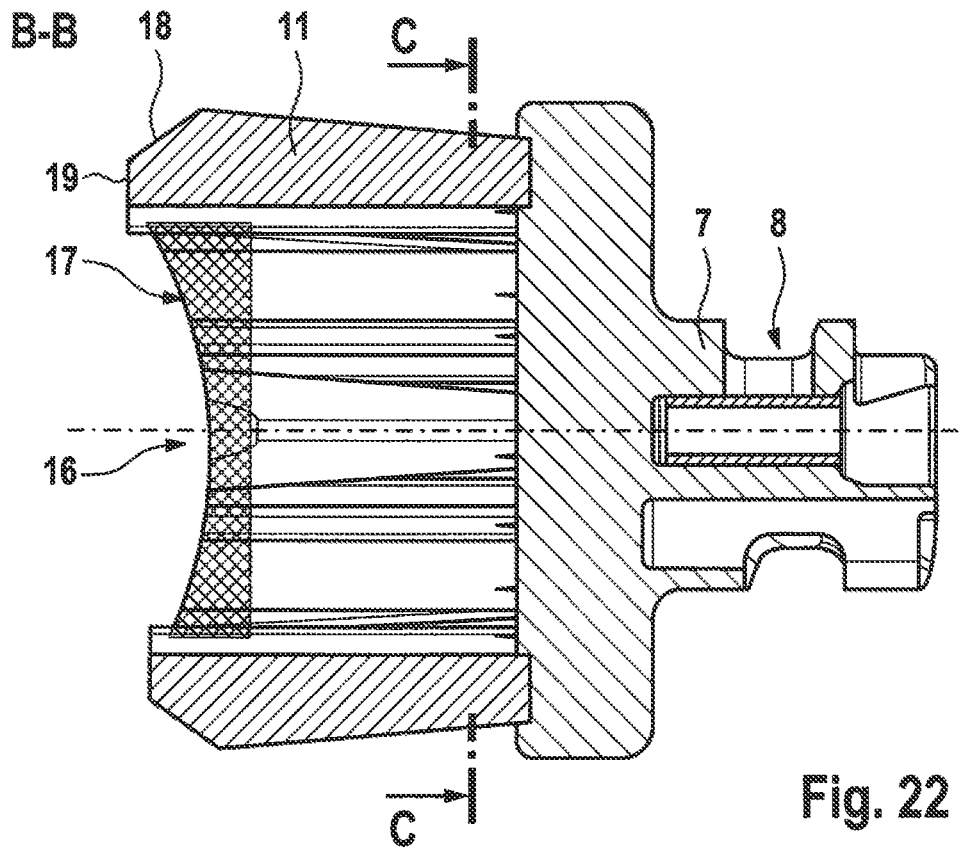
FIG. 22 is a longitudinal sectional view of the toothbrush head taken along the line B-B of FIG. 21 parallel to the longitudinal axis of the toothbrush.
Figure 23:
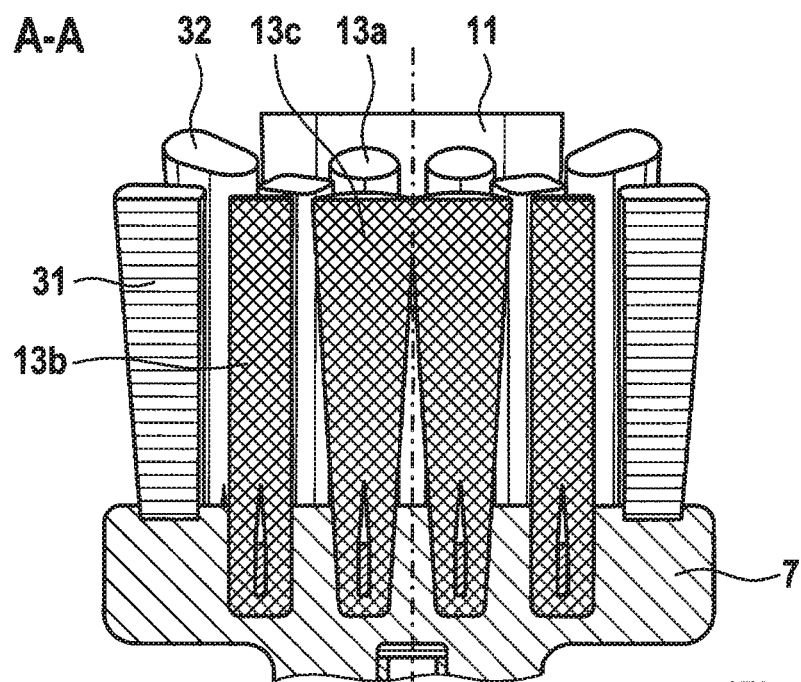
FIG. 23 is a longitudinal sectional view of the brush head taken along the line A-A of FIG. 21.

The embodiment of FIGS. 21 to 23 corresponds substantially to the embodiment of FIGS. 12 to 14 so that reference is made to its preceding description. In the embodiment of FIGS. 21 to 23, the depression 16 relative to the longer outer bristle tufts 11 is made deeper compared to FIGS. 15 to 17, such that a difference in height of 2 mm, approximately, results between the deepest point of the depression 16 and the highest point of the tufts 11.

Figure 24:
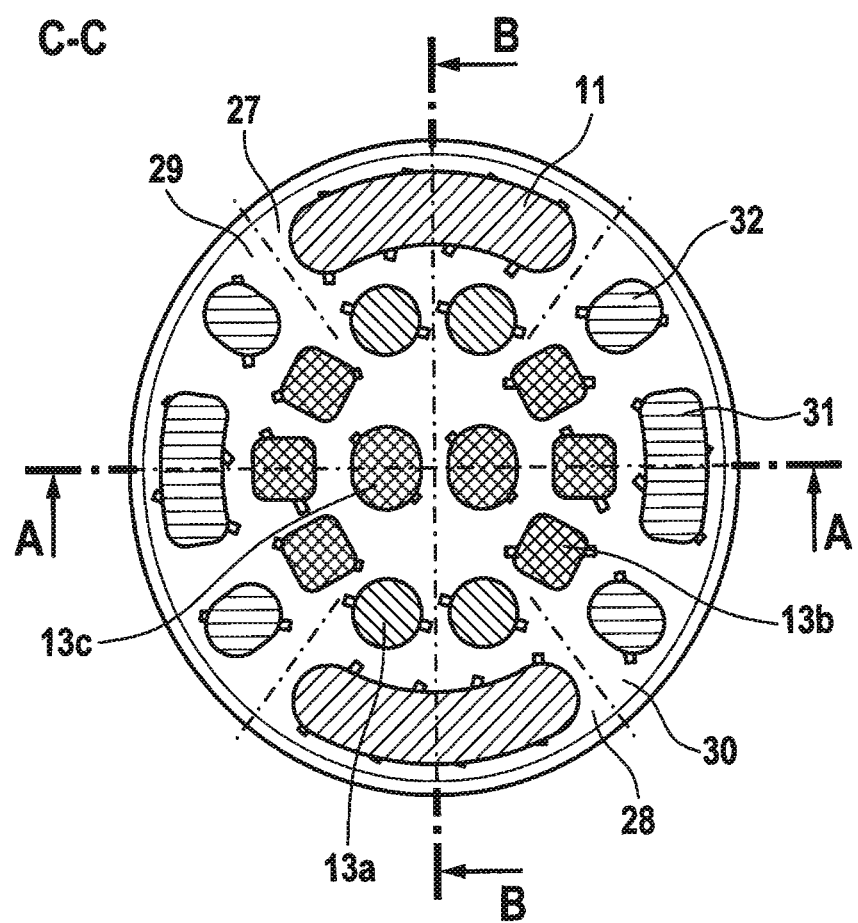
FIG. 24 is a schematic top plan view of the brush head of the toothbrush of FIG. 1 according to another embodiment shown and illustrated herein.
Figure 25:
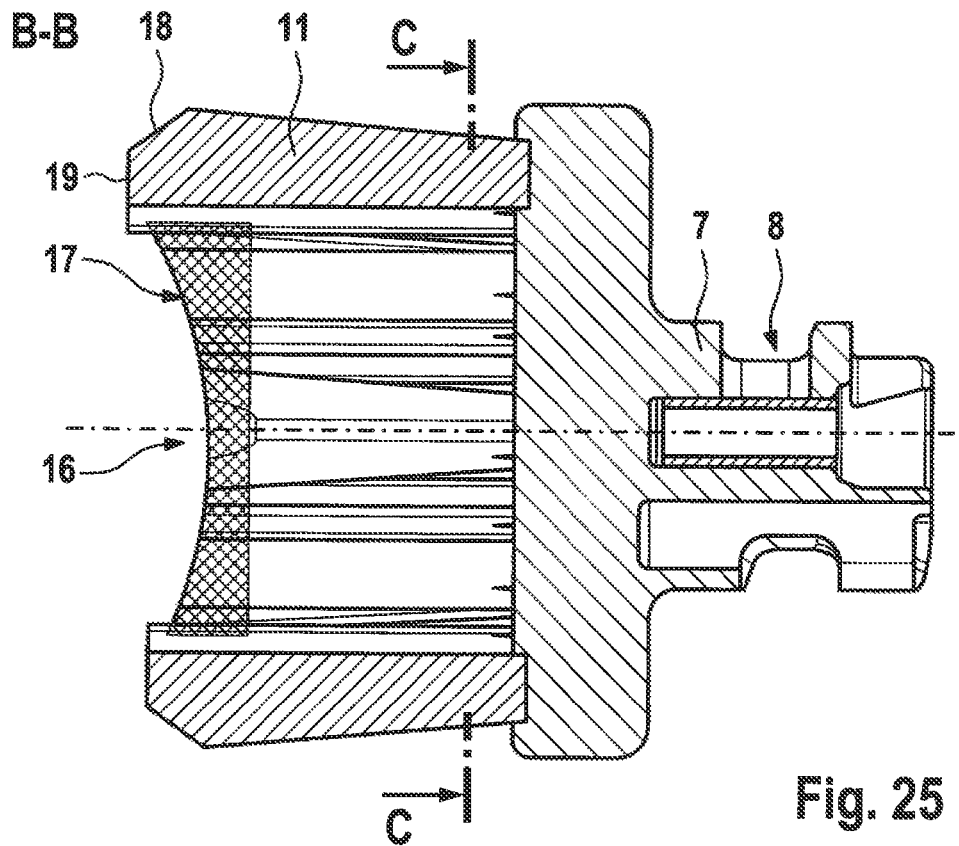
FIG. 25 is a longitudinal sectional view of the toothbrush head taken along the line B-B of FIG. 24 parallel to the longitudinal axis of the toothbrush.
Figure 26:
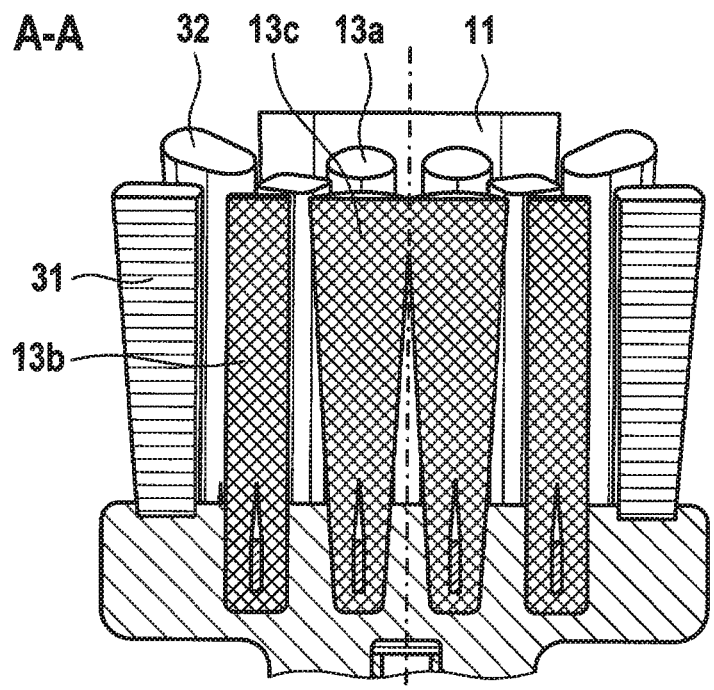
FIG. 26 is a longitudinal sectional view of the brush head taken along the line A-A of FIG. 24.

The embodiment of FIGS. 24 to 26 corresponds substantially to the preceding embodiment of FIGS. 18 to 20 so that reference is made to its preceding description. In contrast to said preceding embodiment, the depression 16 is made deeper relative to the longer outer bristle tufts 11, such that a maximum difference in height of about 2 mm, results.

Figure 27:
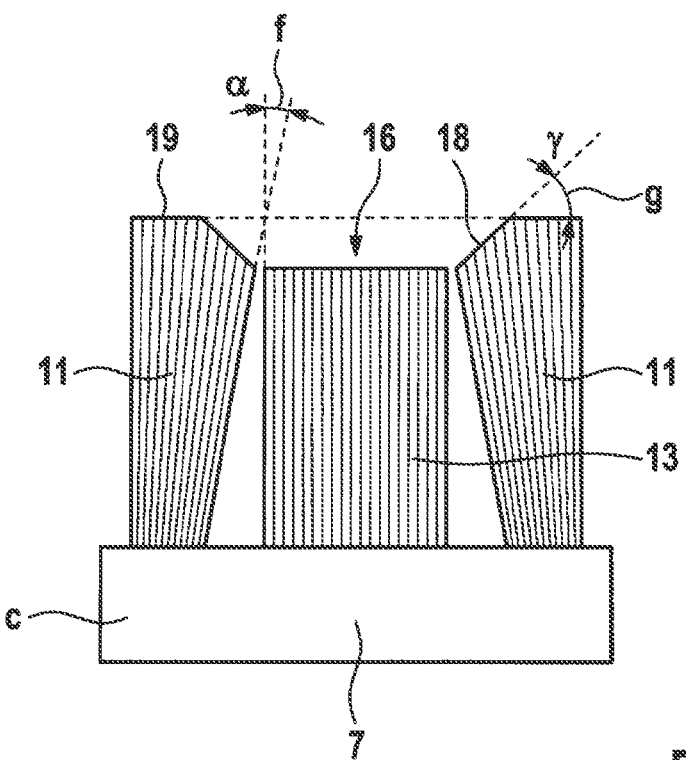
FIG. 27 is a schematic longitudinal sectional view of the brush head of the toothbrush of FIG. 1 according to another embodiment shown and illustrated herein, in which the circumferential outer longer bristle tufts have inner bevels on their outer ends.

As FIG. 27 shows, the longer outer bristle tufts 11, which are arranged in the sectors 27 and 28 in which the longitudinal axis 26 of the toothbrush lies preferably in the non-deflected neutral position of the bristle support 7, can have bevels 18 also on the inner side, that is, on the side close to the axis of rotation, and the width and angle of the bevel 18 can correspond substantially to the previously described geometrical proportions. This applies also for the shorter outer bristles 31 of the sectors 29 and 30. As FIG. 27 shows, said tufts 11 and 31 are likewise of trapezoidal shape, with the beveling being provided however on the inner side, that is, the inner flanks of the tufts 11 are inclined towards a vertical on the bristle support 7 at an acute angle in the range from about 1.5° to about 10° while the outer flanks stand substantially vertically to the bristle support 7.

Figure 28:
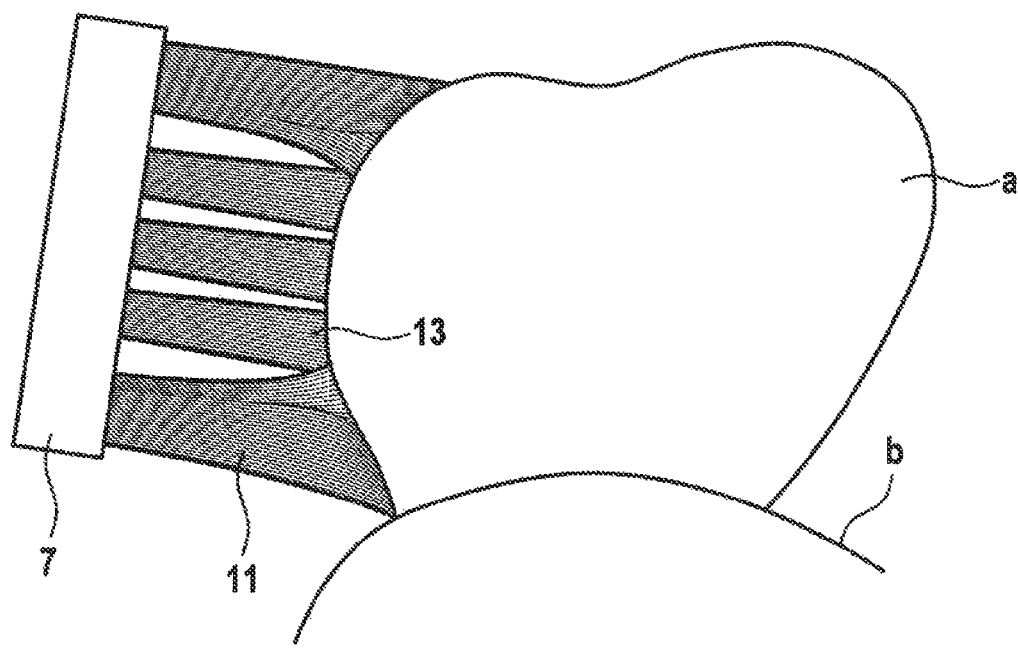
FIG. 28 is a schematic function diagram of the brush head of FIG. 27 showing how the curved working surface of the bristled section hugs a tooth flank.

As FIG. 28 shows, as a result of said bevel 18 on the inner side of the longer outer bristle tufts 11 or shorter outer bristle tufts 31, the free ends of the bristles rest particularly snugly against the cambered tooth flank contour. The variant including the inner bevel in conjunction with shorter outer bristle tufts 31 because of its ability to enhance the cleaning action on the supra-gingival tooth areas.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A brush head for an electric toothbrush comprising:
a bristle support having mounting means for movable mounting of the bristle support; and
a plurality of bristle tufts arranged on the bristle support in at least one outer ring and one middle ring, the middle ring being nested within the outer ring and having a central area;
wherein the plurality of bristle tufts are attached to the bristle support at points of attachment such that there is a continuous, annular bristle free zone located between the outer ring and the middle ring and between the middle ring and the central area;
wherein the outer ring includes outer bristle tufts having an elongated tuft cross-section, which outer bristle tufts are mounted on opposing sides of the outer ring; the middle ring includes at least four middle bristle tufts that each have a cross-section that is smaller than the cross-section of the outer bristle tufts and a central area including at least one bristled section that consists of two center bristle tufts nested within the middle ring and having a cross-section larger than the cross-section of the middle bristle tufts, the center bristle tufts each having an elongated, substantially kidney-shaped form that complement each other so that the bristled section of the central area has an approximately circular, oval or elliptical structure.

2. The brush head according to claim 1, wherein the bristled area within the central area is between about 5% and about 15% of the area of the bristle support.

3. The brush head according to claim 1, wherein the middle bristle tufts have cross-sectional areas of approximately equal size.

4. The brush head according to claim 1, wherein the bristle tufts on the middle ring are of varying cross-sectional shapes.

5. The brush head according to claim 1, wherein the middle bristle tufts comprise rectangular bristle tufts that are arranged on opposing sides of the middle ring and that have an angular cross-section.

6. The brush head according to claim 5, wherein at least one rectangular bristle tuft of the middle ring has its main axis turned in such a way that the main axis is inclined at an acute angle to a tangent to the middle ring, the angle being in the range from about 3° to about 30°.

7. The brush head according to claim 1, wherein the cross-sectional area of the outer bristle tufts and of the at least two center bristle tufts is at least twice as large as the tuft cross-sectional area of a bristle tuft on the middle ring.

8. The brush head according to claim 1, wherein cross-sectional area of the outer bristle tufts varies.

9. The brush head according claim 1, wherein the center bristle tufts have longitudinal axes that extend parallel to each other and/or parallel to a main axis of the bristle support and/or are aligned parallel to a connecting line connecting two opposing outer bristle tufts on the outer ring.

10. The brush head according to claim 1, wherein the bristle support has a round shape selected from oval or elliptical.

11. The brush head according to claim 1, wherein the plurality of bristle tufts, as seen looking at the top of the bristle support, are arranged symmetrically relative to the main axes of the bristle support and/or rotationally symmetrically, in such a way that points of attachment of the bristle tufts on the bristle support are transformable one into the other by a turn through 180°.

12. The brush head according to claim 1, wherein the outer bristle tufts are of greater height than the middle and center bristle tufts, such as to form a central depression in the working surface defined by the free ends of the tufts, with a step-shaped jump in height being provided between the central depression and the outer bristle tufts.

13. The brush head according to claim 1 wherein the mounting means of the bristle support define an axis of rotation for the bristle support suitable for producing an oscillatory rotational motion of the bristle support in a driven state.

14. The brush head according to claim 10, wherein at least one ring of the plurality of bristle tufts defines an oval or an ellipse around the axis of rotation.

\* \* \* \* \*